US00RE38409E

(19) United States
(12) Reissued Patent
Noiles

(10) Patent Number: US RE38,409 E
(45) Date of Reissued Patent: *Jan. 27, 2004

(54) BALL AND SOCKET BEARING FOR ARTIFICIAL JOINT

(75) Inventor: Douglas G. Noiles, New Canaan, CT (US)

(73) Assignee: Joint Medical Products Corporation, Warsaw, IN (US)

( * ) Notice: This patent is subject to a terminal disclaimer.

(21) Appl. No.: 07/191,225

(22) Filed: May 6, 1988

Related U.S. Patent Documents

Reissue of:
(64) Patent No.: 4,678,472
Issued: Jul. 7, 1987
Appl. No.: 06/553,520
Filed: Nov. 21, 1983

U.S. Applications:
(63) Continuation-in-part of application No. 06/473,431, filed on Mar. 8, 1983, now Pat. No. 4,642,123.

(51) Int. Cl.[7] ..... A61F 2/30
(52) U.S. Cl. ..... 623/22.25; 623/23.39
(58) Field of Search ..... 623/16, 18, 19, 623/20, 21, 22, 23

(56) References Cited

U.S. PATENT DOCUMENTS

| | | | | |
|---|---|---|---|---|
| 3,584,318 | A | 6/1971 | Scales et al. | 623/22 |
| 3,683,421 | A | 8/1972 | Martinie | |
| 3,722,002 | A | 3/1973 | Charnley | 623/22 |
| 3,818,512 | A | 6/1974 | Shersher | |

(List continued on next page.)

FOREIGN PATENT DOCUMENTS

| | | |
|---|---|---|
| DE | 7104212 | 5/1971 |
| DE | 2244645 | 3/1974 |
| DE | 2323456 | 11/1974 |
| DE | 2513511 | 10/1975 |

(List continued on next page.)

OTHER PUBLICATIONS

"Original M.E. Müller Pfannendach–Schale," Prospekt PROTEK, 1981.
Greenwood, "Mechanical Details for Product Design," McGraw–Hill Book Co., 1964, pp. 204–205.
Kantorowitsch, "Chemiemaschinen," VEB Verlag Technik, 1970, p. 380.
Richter et al., "Bauelemente der Feinmechanik," VDI–Verlag, 1929, pp. 171–178.
Tourancheau et al., "Éléments de Constuction," Tome II, Dunod, 1965, p. 58.
Charnley, "The Rationale of Low Friction Arhroplasty," in The Hip: Proceedings of the First Open Scientific Meeting of The Hip Society, 1973, Chapter 9, pp. 92–116 (C.V. Mosby Co. 1973).

(List continued on next page.)

*Primary Examiner*—David J. Isabella
(74) *Attorney, Agent, or Firm*—Maurice M. Klee; Richard A. Inz

(57) ABSTRACT

A ball and socket joint for implanting in the body is provided wherein the socket portion of the joint can have various orientations with respect to the patient's anatomy, and the orientation used for a particular patient can be selected and/or changed in situ, that is, during or after implantation of the joint. In addition, the configuration of the joint, e.g., constrained versus semi-constrained, as well as the materials making up the socket portion of the joint, e.g., plastic versus metal, can be selected and/or changed in situ.

REEXAMINATION RESULTS

The questions raised in reexamination request Nos. 90/004, 732, filed Aug. 26, 1997 and 90/005,596, filed Jun. 22, 1999, have been considered and the results are reflected in this reissue.

14 Claims, 10 Drawing Sheets

U.S. PATENT DOCUMENTS

| | | | | |
|---|---|---|---|---|
| 3,829,904 | A | 8/1974 | Ling et al. | |
| 3,868,730 | A | 3/1975 | Kaufer et al. | |
| 3,886,601 | A | 6/1975 | Findlay | |
| 3,894,297 | A | 7/1975 | Mittelmeier | 623/22 |
| 3,903,549 | A | 9/1975 | Deyerle | 623/22 |
| 3,918,102 | A | 11/1975 | Eichler | |
| 3,958,904 | A | 5/1976 | Rusbach | |
| RE28,895 | E | 7/1976 | Noiles | 623/22 |
| 3,996,625 | A | 12/1976 | Noiles | 623/22 |
| 4,004,300 | A | 1/1977 | English | 623/22 |
| 4,040,130 | A | 8/1977 | Laure | 623/22 |
| 4,044,403 | A | 8/1977 | D'Errico | |
| D249,957 | S | 10/1978 | Eicher et al. | |
| 4,150,444 | A | 4/1979 | Hagert | |
| 4,172,296 | A | 10/1979 | D'Errico | 623/22 |
| 4,327,449 | A | 5/1982 | Charnley | |
| 4,352,212 | A | 10/1982 | Greene et al. | 623/22 |
| 4,380,090 | A | 4/1983 | Ramos | |
| 4,404,691 | A | 9/1983 | Buning et al. | |

FOREIGN PATENT DOCUMENTS

| | | |
|---|---|---|
| DE | 2845231 | 5/1979 |
| DE | 2903366 | 8/1979 |
| DE | 2950536 | 7/1981 |
| DE | 81/060262 | 7/1981 |
| EP | 123514 | 8/1981 |
| EP | 65482 | 11/1982 |
| EP | 91315 | 10/1983 |
| FR | 2099259 | 2/1972 |
| FR | 2154246 | 5/1973 |
| FR | 2343919 | 10/1977 |
| FR | 2416004 | 8/1979 |
| FR | 2445909 | 8/1980 |
| GB | 1126961 | 9/1968 |
| GB | 2007980 | 5/1979 |
| GB | 2029230 | 3/1980 |
| GB | 2052620 | 1/1981 |
| GB | 2013503 | 9/1982 |
| GB | 2117646 | 10/1983 |

OTHER PUBLICATIONS

Harris and Oh, "Oh–Harris Protrusio Shell Surgical Technique," Howmedica Surgical Techniques, (Howmedica, 1978).

Oh and Harris, "Design Concepts, Indications, and Surgical Techniques for Use of the Protrusio Shell," Clinical Orthopaedics and Related Research, 162:175–84 (Jan.–Feb. 1982).

Thackray Charnley Bulletin, No. 7 (Chas. F. Thackray Limited, 1982).

Fact sheets re ICTH system, protrusio rings and acetabular cups, with illustrations, DePuy.

Catalog sheets, "A case for conservation: The Indiana Conservative Total Hip", DePuy Inc.

Catalog sheets, "T.A.R.A. Total Hip Systems" and "Indiana Surface Replacement Total Hip Systems," pp. A–30, A–31, A–35 and A–36, DePuy Inc.

Brochure, "Original M.E. Müller Acetabular Roof Reinforcement Ring," Protek Ltd.

Brochure, "protusio acetabuli . . . corrected," DePuy Inc., 1979.

Brochure, "M.E. Müller Total Hip System in Protasul 10," DePuy Inc., 1979.

Brochure, "M.E. Müller Acetabular Roof Reinforcement Rings," DePuy Inc., 1981.

Duff–Barcley et al., "The development of the Stanmore Total Hip Replacement," Proceedings of the Royal Society of Medicine, pp. 948–951.

Wilson, "Problems of Acetabular Fixation in Total Hip Replacement," in "Lubrication and Wear in Living and Artificial Human Joints," The Institution of Mechanical Engineers, Proceedings 1966–67, vol. 181, part 3J, paper 9, pp. 112–120.

Wilson et al., "The Stanmore Metal on Metal Total Hip Prosthesis Using a Three Pin Type Cup," Clinical Orthopaedics and Related Research, vol. 95, Sep., 1973, pp. 239–249.

Dobbs, "Survivorship of Total Hip Replacements," The Journal of Bone and Joint Surgery, vol. 62–B, No. 2, May 1980, pp. 168–173.

Brochure, The Elite Press–Fit Cup, Thackray.

Brochure, Osteonics, 1983.

Brochure, HC1/MC1 Acetabular cups, Osteonics, 1983.

Engineering drawings, DePuy, Inc., 1983–84.

Müller, "Acetabular revision," *The Hip*, Proceeedings of the Ninth Open Scientific Meeting of the Hip Society, 1981, pp. 46–56.

Request For Reexamination, dated Aug. 26, 1997, filed by Smith & Nephew, Inc., Reexam Control No. 90/004,732.

BG total hip prostheses Lord Madreporique literature.

Lord et al., "The Madreporic Cementless Total Hip Arthroplasty: New Experimental Data and a Seven–year Clinical Follow–up Study," 176 *Clinical Orthopaedic and Related Research*, Jun. 1983, pp. 67–76.

Lord et al., "An Uncemented Total Hip Replacement: Experimental Study and Review of 300 Madreporique Arthroplasties," 141 *Clinical Orthopaedics and Related Research*, Jun. 1979, pp. 2–16.

Lord et al., "Pour un ancrage biologique sans ciment des arthroplasties totals de hanche: Premier bilande 200 protheses madreporiques" ["For a cement–free biological fixation of total hip protheses: First results of 200 madreporic prostheses"], S.O.F.C.O.T. Annual Meeting, Nov. 1977 (Supp. II, Rev. Chir. Orthop. 1978, 64) (original and translation).

Engineering drawings, DePuy, Inc., 1983–84.

Richards et al., "Biology Response to Uncemented Madreporic Canine Hip Arthroplasty," *The Canadian Journal of Surgery*, vol. 30, No. 4, Jul., 1987, 245–48.

Pipino and Calderale, "Biodynamic Total Hip Prosthesis," *Italian Journal of Orthopaedics and Traumatology*, vol. XIII, No. 3, Sep. 1987.

Pipino and Calderale, "La Protesi Biodinamica Totale D'Anca," *Giomale Italiano di Ortopedia e Traumatologia*, Sep. 1987, 299–307.

Calderale, progettazione biomeccanica, *Il Progrettista Industriale*, 2/82, 82–91.

A draft Howmedica brochure for the biequatorial cup.

Molfetta et al., "Studio Radiografico Della Morfometria Dell'Anca," *Minerva Ortopedica E Traumatologica*, 1–5.

Pipino et al., "Criteri di valutazione clinica dei pazienti con artroprotesi d'anca," *Minerva Ortopedica E Traumatologica*, vol. 37, Nov. 1986, 699–701.

Pipino et al., "La Protesi D'Anca Biequatoriale," *La Patologia non Traumatica dell'Anca*, Chapter XXXIII, 1984, 325–33.

Quagliarella et al., "Determinazione della superficie articolare cotiloidea nella protesi d'anca biequatoriale," *Minerva Ortopedica*, vol. 35, 1984, 3–8.

Pipino et al., "Valutazione biomeccanica sulla opportunitá di impiego delle protesi madreporiche con cemento acrilico," *Minerva Ortopedica*, vol. 35, 1984.
Pipino and Calderale, "Una coppa acetabolare biequatoriale per la protesi dell'anca," *Minerva Ortopedica*, vol. 30, 1979.
Pipino and Calderale, Howmedica brochure, "Protesi Totali D'Anca Biodinamica".
"Howmedica News".
Pipino (ed.), "Atlas Of Orthopedic Surgery, Third Volume, The Biodynamic Total Hip Prosthesis With a Biequatorial Cup, 1990".
Baumeister, T. et al., *Mechanical Engineers Handbook*, McGraw–Hill, New York, pp. 8–48, 1958.
Gilula, L. et al., *Radiologic Clinics of North America*, vol. 13, pp 21, 41–43, Apr. 1975.
Harris, William H., "A New Total Hip Implant," Clinical Orthopaedics and Related Research, No. 81, Nov.–Dec., 1971.
Pipino and Calderale, "A biequatorial acetabular cup for hip prosthesis," *Acta Orthopaedica Belgica*, vol. 46, pp. 5–13 (1980).
Pipino and Calderale, "A biequatorial hip prosthesis," *Pan. Med.*, vol. 25, pp. 231–238 (1983).
Woo, R. et al., *The Journal of Bone and Joint Surgery*, vol. 64–A, Dec. 1982, pp. 1295–1306.
"Buck 32 Total Hip Replacement," Richards Manufacturing Company, Inc., Memphis, Tennessee, 1981.
"Charnley Round Back," Codman and Shurtleff, Inc., Randolph, Massachusetts, 1978.
Total Hip Replacement, Richards Manufacturing Company, Inc., Memphis, Tennessee, 1979.
*Vitallium Harris Total Hip System*, Howmedica, Inc., Rutherford, New Jersey.
Steindler, A., *Kinesiology*, Charles C. Thomas, Springfield, Illinois, 1955, pp. 287–289.
"Universal Acetabular Cup System—Surgical Procedures . . . " DePuy, Warsaw, Indiana, 1987.
"Universal Acetabular Cup System—Implant Options for Virtually Any Acetabular Reconstruction", DePuy, Warsaw, Indiana, 1987.
"The P.C.A. Acetabular Cup System", Howmedica, Rutherford, New Jersey, 1986.
"ACCU–Path—Acetabular Cup System from Howmedica", Howmedica, Rutherford, New Jersey.
OPTI–FIX and TI–FIT advertisements, Richards Medical Company, Memphis, Tennessee, 1986.
Engh et al., *Biological Fixation in Total Hip Arthroplasty*, SLACK Incorporated, Thorofare, New Jersey, 1985.
Contemporary Orthopaedics Sixth Bi–Annual Market Survey.
*Total Hip Technique*, DePuy Division of Bio–Dynamics, Inc., Warsaw, Indiana.

BALL AND SOCKET BEARING FOR ARTIFICIAL JOINT

Matter enclosed in heavy brackets [ ] appears in the original patent but forms no part of this reissue specification; matter printed in italics indicates the additions made by reissue.

CROSS REFERENCE TO RELATED APPLICATION

This is a continuation-in-part of copending application Ser. No. 473,431, filed Mar. 8, 1983 no U.S. Pat. No. 4,642,123.

BACKGROUND OF THE INVENTION

1. Field Of The Invention

This invention relates to artificial joints and in particular to artificial joints of the ball and socket type.

2. Description Of The Prior Art

As is well known in the art, artificial hip and shoulder joints conventionally employ ball and socket articulations. The socket is embedded in one bony structure, for example, the pelvis for a hip reconstruction. The ball is attached to an arm composed of a neck and a stem or shaft, the stem or shaft being embedded in another bony structure, for example, the femur for a hip reconstruction.

A number of methods are known for retaining the ball in the socket. In the most common method, referred to herein as the "semi-constrained" construction, the patient's own anatomy, i.e., his muscles, tendons and ligaments, are used to retain the ball within the socket. For this construction, a hemispherical socket typically is used which allows the ball and its attached arm the maximum amount of movement without contact of the arm with the edge of the socket. The surgeon, when installing such a semi-constrained joint, aligns the ball and socket as closely as possible with the patient's natural anatomy so that the patient's movements do not tend to dislocate the ball from the joint. As a general proposition, such precise alignment is easiest the first time an artificial joint is placed in a patient. Subsequent reconstructions are much more difficult to align because of deterioration of anatomical landmarks as a result of the first operation, the healing process after the operation and changes in the anatomy caused by the presence of the artificial joint.

In order to increase the inherent stability against dislocation of such semi-constrained constructions, it has become conventional to add a cylindrical portion to the hemispherical socket to make it deeper. Although the ball is not physically constrained by the socket by this adjustment, the ball does not have further to travel than if just a hemisphere had been used and thus some reduction in the propensity towards dislocation is achieved. Ball and socket joints of this type generally provide an arc or range of motion of approximately 115° when a 28 mm diameter sphere is used and the socket is made a few millimeters deeper than a hemisphere. Larger ranges of motion can be obtained by keeping the size of the arm attached to the ball constant and increasing the diameter of the ball. In this way, the angular extent of the arm relative to the ball becomes smaller. In the limit, if the ball could be made progressively larger and larger, a range of motion of 180° could be achieved. In practice, however, the largest sphere in common use in artificial joints, and in particular artificial hip joints, has a diameter of 32 mm and provides a range of motion of approximately 120°. It should be noted however, that such larger sphere sizes are not universally favored because frictional torque increases with diameter.

A recent study by the Mayo clinic, which appeared in December, 1982 edition of The Journal of Bone and Joint Surgery, reported a dislocation frequency of 3.2% for 10,500 hip joint implant procedures using the semi-constrained construction. Such dislocations essentially make the patient immobile and can necessitate a second operation. As discussed above, the critical alignment required for the semi-constrained construction is even more difficult to achieve when a second implantation is performed. Accordingly, even higher dislocation frequencies are encountered for second and subsequent implantations.

An alternative to the semi-constrained construction is the construction wherein the ball is physically constrained within the socket. In this construction, a spherically-shaped bearing surrounds the ball and serves as the socket. The bearing is attached to a fixation element which is embedded in, for example, the patient's pelvic bone. The bearing encompasses more than one-half of the ball and thus constrains the ball and its attached arm from dislocation.

The bearing is typically made from plastic, such as ultra-high molecular weight polyethylene (UHMWPE), or metal. For plastic bearings, the ball and bearing are usually assembled by forcing the bearing over the ball. The more of the ball which is encompassed by the bearing, the greater the required assembly force, and the greater the constraining force to prevent postoperative dislocation of the joint. In addition, the more that the bearing encompasses the ball, the smaller the range of motion for the ball prior to contact of the bearing with the arm attached to the ball.

An example of a constrained artificial joint employing a plastic bearing is shown in Noiles, U.S. Pat. No. 3,996,625. As can be seen in FIG. 1 of this patent, a plastic bearing 17 fitted with a metal reinforcing band (un-numbered) extends beyond the diameter of ball 24 so as to physically constrain the ball within the bearing. The bearing itself is attached to fixation element 12. The metal reinforcing band is assembled over the lip of the opening of bearing 17 after that bearing has been forced over sphere 24. The reinforcing band increases the force required to dislocate the joint. In practice, the design shown in FIG. 1 of U.S. Pat. No. [3,966,625] *3,996,625* has been found to provide a range of motion of approximately 85° when a sphere diameter of 28 mm is used and to resist direct dislocating forces of several hundred pounds.

For constrained constructions such as that shown in U.S. Pat. No. 3,996,625, it has been found in use that a dislocating force is created when the neck of the arm attached to the ball impinges on the rim of the bearing. Because of the leverage associated with the arm and the long bone of the patient to which it is attached, e.g., the patient's femur, the dislocating force produced when the neck contacts the rim of the bearing can be considerable. For example, a force on the order of 25 pounds applied to a patient's leg can produce a dislocating force of over several hundred pounds because of the leverages involved. This type of dislocation force can be avoided by geometrically aligning the artificial joint with the patient's anatomy so that the neck does not come in contact with the rim of the bearing during normal motion of the patient's limb. That is, the leverage based dislocation forces can be avoided in the same way as dislocations are avoided in the [seim-constrained] *semi-constrained* construction, i.e., through precise alignment of the artificial joint with the natural anatomy of the patient. Unfortunately, as is apparent from the geometry of the situation, the more the socket bearing encompasses the ball, the greater the restraining force on the ball, but at the same time the less the range of motion prior to the neck impinging upon the edge of the bearing to create undesired leverage. In practice, artificial hips having the construction shown in U.S. Pat. No. 3,996,625 have been found to suffer dislocation due to the leverage effect in fewer than 0.5% of the implantations performed. This is significantly better than the 3.5% dislocation frequency reported in the Mayo clinic study discussed above, but an even lower dislocation frequency is obviously desirable.

A constrained construction using a metal socket bearing is shown in Noiles, U.S. Pat. Re. 28,895 (reissue of U.S. Pat. No. 3,848,272). This construction provides approximately a 90° range of motion where the sphere diameter is 28 mm. In a practical sense, the metal bearing can be said to be non-dislocatable. The force required to extract the metal sphere from the enclosing metal socket bearing is more than several thousand pounds. Accordingly, is use, rather than the metal ball dislocating from the metal socket bearing, any overly severe dislocating leverage will cause the fixation element to be disrupted from the bone in which it has been embedded.

As a general proposition, metal balls in metal socket bearings are used in only a minority of joint reconstructions because the medical profession is not in agreement that a metal sphere in a metal bearing is as biologically acceptable as a metal sphere in a UHMWPE plastic bearing, even though clinical use over 15 years has failed to show the metal to metal joint to be inferior to a metal to plastic joint.

A third type of artificial ball and socket joint, referred to as an endoprosthesis, eliminates the fixation element associated with the socket and simply uses a ball surrounded by a plastic socket bearing in a spherical metal head, which head is placed in the patient's natural socket but not secured to bone. For this construction, the ball can rotate within the bearing up to the rim of the bearing (the bearing is greater than a hemisphere so as to be retained on the ball), and then the bearing and its attached head rotates in the patient's socket. As with the semi-constrained construction, anatomical alignment is used to avoid dislocations, in this case between the metal head and the natural socket.

In view of the foregoing, it is apparent that in semi-constrained and endoprosthesis hip joints, reconstructive geometry of the prosthesic components is critical in ensuring the stability of the prosthesis against dislocation. Moreover, in ball and socket constructions which constrain the elements against dislocation, the range of motion inherent in the prosthesis is reduced and thus because of the possibility of leverage type dislocations, similar demands are placed on the surgeon to establish the geometry of the reconstruction within rather narrow limits.

Accordingly, an object of this invention is to provide a ball and socket joint which provides the surgeon with increased latitude in geometric positioning of the prosthetic components over those ball and socket joints presently available.

A further object of the invention is to provide a ball and socket joint the materials and configuration of at least a portion of which can be selected and/or changed in situ, that is, during or after implantation of the joint in the patient.

An additional object of the invention is to provide a ball and socket joint including a bearing member which can be readily replaced in situ with either a bearing member of the same or of a different type depending on the patient's post-operative history.

Another object of the invention is to provide a ball and socket joint wherein (1) the socket portion of the joint has more than one orientation with respect to the ball portion of the joint, the preferred orientation being a function of the patient's anatomy, and (2) the orientation of the socket portion with respect to the ball portion can be selected and/or changed in situ, that is, during or after implantation of the joint in the patient.

A further object of the invention is to provide a prosthetic ball and socket joint of increased inherent range of motion which is readily assembled and disassembled at the surgical site.

An additional object of the invention is to provide a ball and socket bearing for an artificial joint which constrains the joint from dislocating and at the same time provides a range of motion which is greater than that available in the construction of the constrained type described above.

SUMMARY OF THE INVENTION

To achieve these and other objects, the invention, in accordance with one of its aspects, provides a ball and socket joint for implantation in a patient's body comprising a ball portion and a socket portion, the ball portion including:

a ball; and first fixation means for implantation in a first bony structure, said fixation means being connected to said ball; and the socket portion including:

a bearing for receiving the ball; said bearing defining an orientation between itself and the patient's body;

second fixation means for implantation in a second bony structure; and connecting means associated with the bearing and the second fixation means for connecting the bearing to the second fixation means in more than one orientation.

In accordance with a further one of its aspects, the invention provides a ball and socket joint for implantation in a patient's body comprising a ball portion and a socket portion, the ball portion including:

a ball; and first fixation means for implantation in a first bony structure, said fixation means being connected to said ball; and the socket portion including:

a bearing for receiving the ball, said bearing being one member of a family of interchangeable bearings, the family including at least one member which is made from a different material or which has a different configuration or which is both made from a different material and has a different configuration from at least one other member of the family;

second fixation means for implantation in a second bony structure; and connecting means associated with the bearing and the second fixation means for interchangeably connecting any bearing in the family to the second fixation means.

In accordance with an additional one of its aspects, the invention provides a ball and socket joint for implanting in the body which comprises:

a ball;

a cup with a spherical cavity, said cup to be affixed to bone; and a bearing member surrounding a portion of the ball and rotatable within said spherical cavity about only one axis, said bearing member having an asymmetric opening therein, the opening having an angular extent of less than 180° in at least one plane.

In accordance with another one of its aspects, the invention provides an artificial joint of the ball and socket type for implantation in the body which comprises:

a ball;

a bearing for forming a socket to receive the ball, the bearing having an asymmetric opening therein, the opening having an angular extent of less than 180° in a first plane;

means for pivoting the bearing about an axis lying in a plant other than the first plane; and means for affixing the means for pivoting to bone.

In accordance with another of its aspects, the invention provides a socket for a ball and socket joint for implantation in the body which comprises (1) a cup with a cavity, and (2) a bearing for receiving the ball of the ball and socket joint, said bearing being constrained to rotate within said cavity about a single axis.

In accordance with certain preferred embodiments of the invention, the asymmetric opening into the sockets is less in one direction than it is at 90° to this one direction. The socket bearing is movably retained within the cup about an axis which is (1) parallel to the face of the cup and (2) in the direction of the greater opening in the socket bearing. The socket bearing is retained within the cup by two stub half round pins integral with the cup and extending part way through the wall thickness of the socket. The axes of the half round pins coincide with an axis of the spherical cup like cavity and they are also coaxial in the direction of the greater opening in the socket bearing.

When the ball and the neck of the arm of the prosthesis move in the direction of the lesser opening in the socket bearing, the total range of motion is the sum of the arc of motion which the neck can make within the bearing plus the arc of motion which the bearing can make within the cup. The cup can be a hemisphere or even less. Rotation of the ball is limited by impingement of the neck against the rim of the cup, or alternatively, and most preferably, by limiting the rotation of the socket bearing so that the neck comes just up to, but not actually into contact with, the rim of the cup. In this regard, reference is made to copending U.S. patent application Ser. No. 553,518 to Alfred Frederick DeCarlo, Jr., filed simultaneously herewith and assigned to the assignee of the present application. This application, the pertinent portions of which are incorporated herein by reference, discloses a preferred system for limiting the rotation of the socket bearing to keep the neck of the arm of the prosthesis out of contact with the rim of the cup.

When the diameter of the ball is approximately the 28 mm in common use, and the socket bearing wall thickness is approximately 7 mm, the inner diameter of the cup, and thus the outer diameter of the bearing, is approximately 42 mm (28 mm+7 mm+7 mm). This outer diameter for the bearing is larger than the largest diameter sphere commonly used in semi-constrained artificial hip replacements, and thus the present constrained construction achieves a greater range of motion than the semi-constrained construction, and at the same time, restrains the ball within the socket.

When the ball and the neck move in the direction of the greater opening in the socket bearing, the neck contacts the flat side of a stub half round pin, rather than the rim of the cup, or alternatively, and most preferably, a web portion of the socket bearing in the region of the stub half round pins (see, for example, element 106 in FIGS. 13, 15 and 21 below). To allow the neck and ball to move through the same arc in this direction, the flat sides of the pins can be contoured. With this feature, the total range of motion in all quadrants, using the above dimensions, is approximately 135°.

To summarize, in accordance with the above preferred embodiments of the invention, when motion is in the plane of the stub pins, the total motion is by movement of the ball within the bearing. When motion is at 90° to the plane of the pins (the "90° plane"), the total motion is the sum of the motion of the ball within the bearing and the motion of the bearing within the cup. In other planes, the motion of the ball within the bearing is greater than it is in the 90° plane and the motion of the bearing within the cup is less than it is in the 90° plane. In this way, the invention provides a constrained ball and socket prosthesic joint with a total range of motion significantly greater than hitherto generally available.

In connection with artificial hip joints, it is advantageous to orient the cup in situ so that the axis of the stub pins is inclined according to the anatomical requirements of the patient as determined by the surgeon. For example, the axis can be inclined somewhat upward in the forward direction. In this manner almost all highly repetitive load bearing motions of the hip joint fall within the motion capability of the sphere within the socket bearing. Additional motion is furnished by movement of the bearing within the cup in such activities as crossing the legs when seated, or in significant abduction. To conveniently permit such orientation of the stub pins, in certain embodiments of the invention, the cup includes first and second portions, the first portion to be affixed to bone, the second portion having associated therewith the pin members are being moveable with respect to the first portion to provide a plurality of possible orientations for the axis of rotation of the bearing member within the spherical cavity.

In connection with both artificial hip joints and other types of ball and socket joints, it is advantageous for the surgeon to have as wide a range of joint configurations and materials to choose from as possible. It is particularly advantageous for the surgeon to be able to refine his selection of materials and configurations during the operative procedure, after he has seen the diseased joint and has a full appreciation of the patient's medical condition and anatomy. Along these same lines, it is also advantageous to be able to re-operate and change materials and/or joint configurations as a function of the patient's post-operative history without substantially disturbing the established fixation of the joint to bony structures. For example, a patient originally fitted with a semi-constrained joint may be found to be especially prone to dislocations so that a constrained construction, perhaps including a metal socket, would be more appropriate.

To achieve these types of flexibility, in accordance with certain preferred embodiments of the invention, a family of interchangeable socket bearings of different configurations and/or materials is provided to the surgeon. Each of the bearings includes means for interchangeably connecting the bearing to a fixation element for the socket portion of the joint in such a way that the bond between the fixation element and the patient's bone is not substantially disturbed by the connecting process. In view of this easy interchangeability, during the initial operation, the surgeon need not choose the specific socket bearing to be used until after completing the implantation of the fixation element, and during subsequent operations, if any, he can substitute a different bearing or replace a worn bearing without breaking the bond between the fixation element and the patient's bone.

In the description of the preferred embodiments which appears below, constructions are shown using both plastic and metal socket bearings, as well as bearings employing a combination of metal and plastic components. Also, various assembly and disassembly constructions are illustrated. It is to be understood, of course, that both the foregoing general description and the following detailed description are explanatory only and are not restrictive of the invention.

The accompanying drawings, which are incorporated in and constitute part of the specification, illustrate the preferred embodiments of the invention, and together with the description, serve to explain the principles of the invention.

DESCRIPTION OF THE PREFERRED EMBODIMENTS

Figure 1:
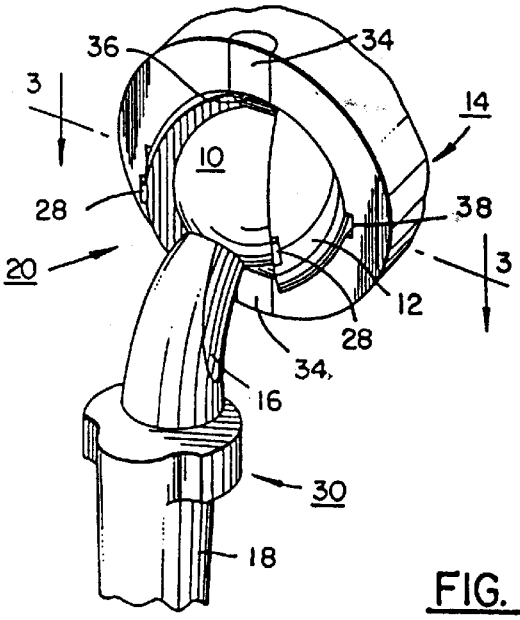
FIG. 1 is a perspective view of an artificial joint embodying the present invention.

With reference now to the drawings, wherein like reference characters designate like or corresponding parts throughout the several views, there is shown in FIG. 1 an assembly 20 of ball or sphere 10, socket bearing 12 and cup 14 for a prosthetic joint. The neck 16 of arm 30 is intermediate ball 10 and stem or shaft 18, which stem or shaft is fixed to, for example, the femur bone at the time of implant surgery.

Figure 2:
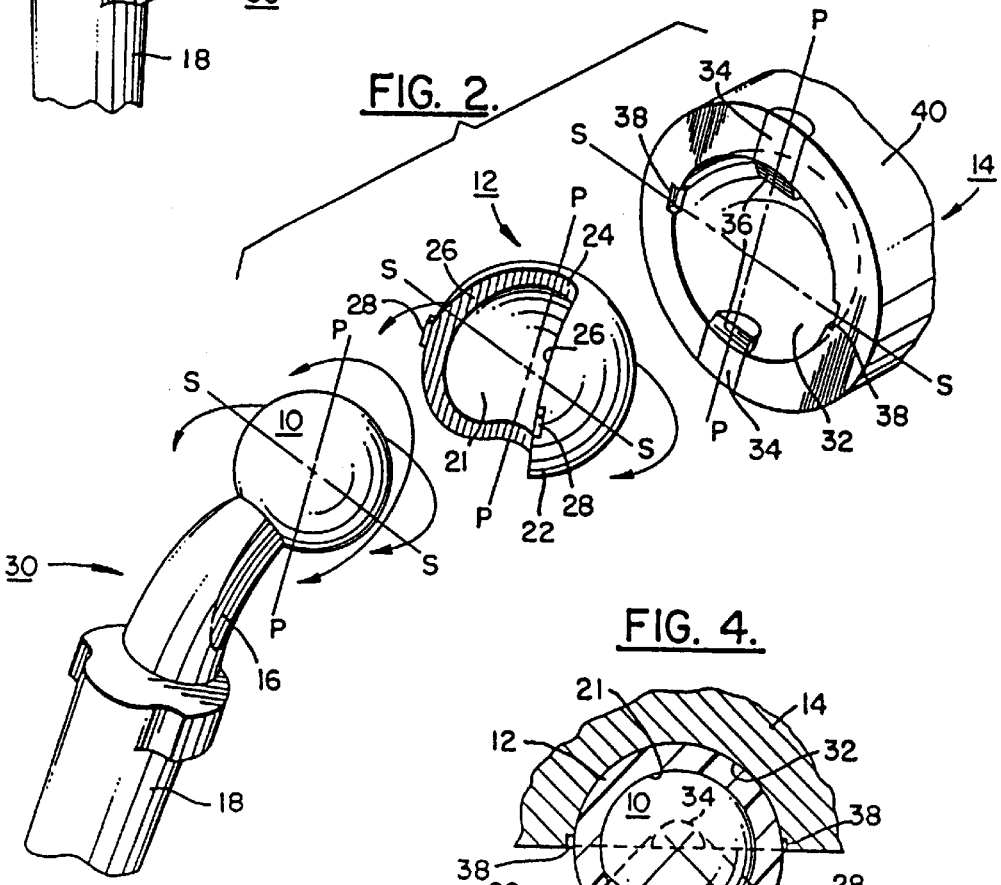
FIG. 2 is an exploded view showing the components of the joint of FIG. 1.

FIG. 2 shows in more detail socket bearing 12 of assembly 20. The preferred material for bearing 12 is ultra-high molecular weight polyethylene (UHMWPE). Inner spherical bearing surface 21 of bearing 12 is concentric with outer spherical bearing surface 22. Cylindrical surfaces 24 are coaxial with each other and with the center of spherical surfaces 21 and 22 and are tangent to surfaces 26. Small barb-shaped protuberances 28 serve a detent function described below.

In the plane passing through the lines P—P in FIG. 2, socket bearing 12 encompasses less than one half of ball 10. In the plane passing through the lines S—S, the socket bearing encompasses more than half of ball 10.

Owing to the resilience and elasticity of the plastic material of socket bearing 12, socket bearing 12 can be snapped over ball 10. The amount of interference between the equator of the ball and socket bearing 12 depends on the angular extent of the bearing's opening in the plane passing through the lines S—S in FIG. 2. [the] *The* amount of interference should be such as will cause an elastic deformation of socket bearing 12 while the bearing is being assembled over the ball 10. To aid in assembly, socket bearing 12 can be heated to a non-destructive temperature (for example 70°–80° C. for UHMWPE). Plastic in general, and UHMWPE in particular, has a large coefficient of thermal expansion and such thermal expansion due to heating significantly aids in assembly.

As shown in FIG. 2, cup 14 has a hemispherical inner surface 32 and two coaxial stub half pin members 34 which are structurally integral with cup 14. The pins 34 are shown bevelled at 36. Recesses 38 are provided at the inner rim of the cup at locations 90° displaced from the pins 34. The exterior surface 40 of cup 14 is of any conventional contour for fixation in bone whether by use of cement, or without cement by means of impaction, screwing in, or by bone ingrowth into porous metal or the like. Cup 14 is normally made of metal, and it is to be understood that the metal used is to be structurally and biologically suitable for surgical implantation.

Figure 3:
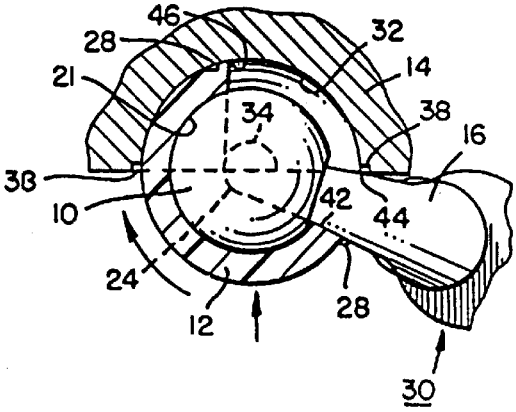
FIG. 3 is a cross-sectional view along lines 3—3 in FIG. 1 showing the ball and the socket bearing partially inserted into the cup.

A step midway in the process of assembly is schematically shown in FIG. 3 where bearing 12 has been positioned against neck 16 at 42 and the bearing 12 and arm 30 have been inserted into cup 14 with neck 16 contacting the rim of cup 14 at 44. Cylindrical surface 24 of bearing 12 engages stub pin 34 as the entering rim 46 of bearing 12 contacts inner surface 32 of cup 14. At this time the bearing 12 is pressed firmly enough into cup 14 to compress protuberance 28, allowing bearing 12 to be rotated clockwise about ball 10 and pin 34 while it is in contact with inner spherical surface 32.

When bearing 12 has been rotated sufficiently for protuberance 28 adjacent rim 46 to reach recess 38, protuberance 28 expands to resist rotation in the reverse direction and thereby resist disassembly of the ball and socket joint 20 unless a tool is inserted into recess 38 to again compress protuberance 28 as rotation in the disassembly direction is started.

The assembled joint is shown in FIG. 1, where the neck 16 of arm 30 can move through the arc from the position shown to that which is symmetrically opposite. That is, the neck of the prosthesis can move in the plane through lines P—P of FIG. 2 from a position of contact with lower stub pin 34 to contact with upper stub pin 34. When ball 10 has a diameter of 28 mm and the outer diameter of bearing 12 is 42 mm, the arc or range of motion of neck 16 is somewhat greater than 135°, depending on the design of the neck 16.

Figure 4:
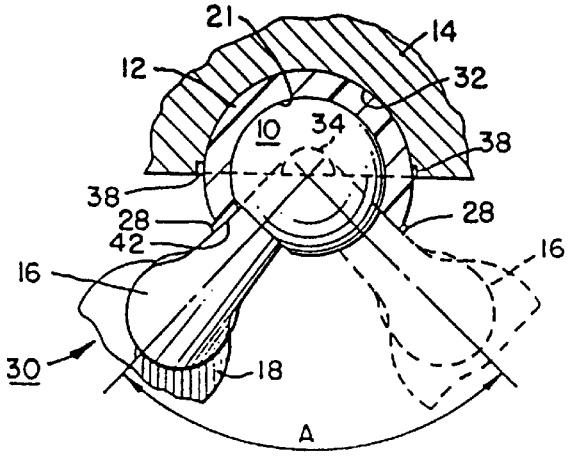
FIG. 4 is a cross-sectional view along lines 3—3 of FIG. 1 showing the range of motion of the ball within the socket bearing with the socket bearing stationary.
Figure 5:
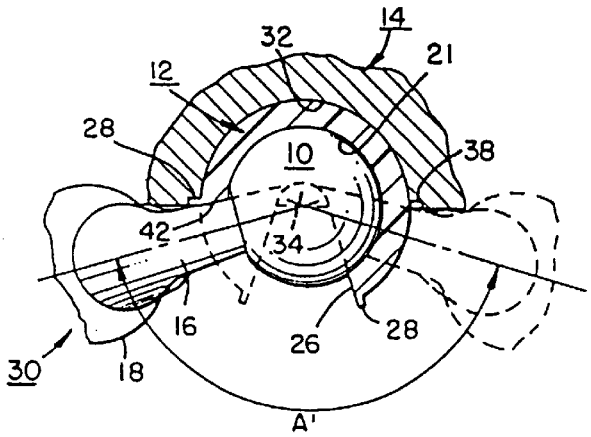
FIG. 5 is a cross-sectional view along lines 3—3 of FIG. 1 showing the range of motion of the ball within the socket bearing when the socket bearing moves within the cup.

To achieve this same range of motion in the plane through lines S—S in FIG. 2 requires two motions. First, as shown in FIG. 4, the neck 16 and ball 10 move through the angle A by the ball 10 turning inside the socket bearing 12, at the completion of which neck 16 contacts the rim of bearing 12. Thereafter, as shown in FIG. 5, to achieve the full range of motion A', ball 10 and bearing 12 rotate in unison, at the completion of which neck 16 contacts cup 14.

Normally, until neck 16 reaches the rim of socket bearing 12, socket bearing 12 will remain stationary relative to cup 14. This is so because frictional torque is the product of friction force times the distance from the center of rotation. Given similar materials, finish and geometric accuracy, so that the coefficient of friction for ball 10 and cup 14 against bearing 12 are equal, the frictional force on inner surface 21 will be the same as that on outer surface 22 when ball 10 rotates within cup 14, because the load transmitted across the two bearing surfaces is the same. Since the radius to the outer surface 22 is the greater, the frictional torque at the outer surface will be greater and thus motion will occur along surface 21 rather than surface 22.

For major oscillation of ball 10 and neck 16 in the plane through lines P—P in FIG. 2, the entire excursion is due to rotation of ball 10 within bearing 12. The total possible oscillation in all planes is the same, however, the contribution made by rotation of bearing 12 increases as the plane of oscillation moves from that including the lines P—P to that including the lines S—S in FIG. 2.

As described above, bearing 12 constrains ball 10 from dislocation. Further, socket bearing 12 is constrained within cup 14 by cylindrical surfaces 24 being journaled by the stub half pins 34 in all positions of bearing 12 as bearing 12 moves to allow arm 30 to move through angle A'. In the complete assembly 20, the constraint against dislocation of ball 10 by deformation of plastic bearing 12 is greater in magnitude than the force required to assemble bearing 12 over ball 10 because, in addition to the fact that the assembly operates at the body temperature of 37° C., the bearing 12 is now itself constrained against the deflection of dislocation by being captured within metal cup 14.

Figure 6:
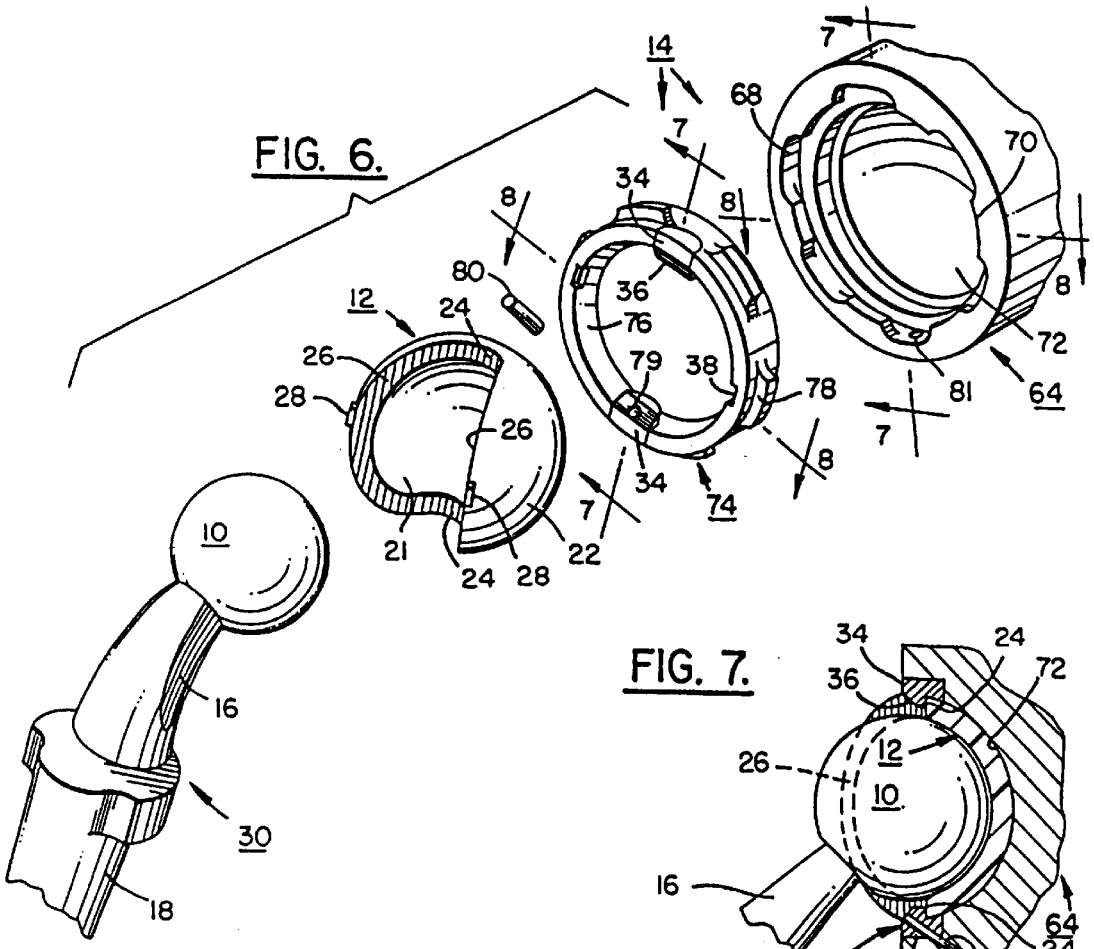
FIG. 6 is an exploded view of an alternate embodiment of the invention wherein the cup includes two portions which are moveable relative to each other.
Figure 7:
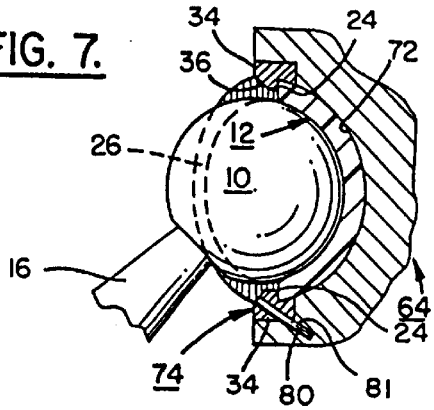
FIG. 7 is a cross-sectional view along lines 7—7 in FIG. 6 after the joint has been assembled.
Figure 8:
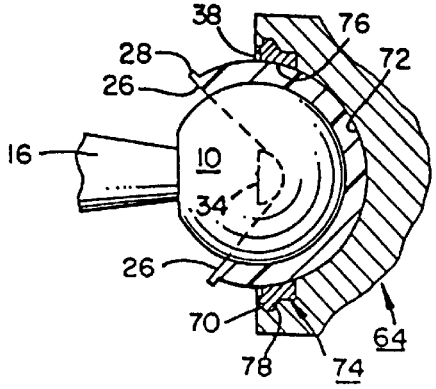
FIG. 8 is a cross-sectional view along lines 8—8 in FIG. 6 after the joint has been assembled.

FIGS. 6, 7 and 8 show an alternate construction intended to (1) facilitate final assembly at the operative site, and (2) for hip joint replacements, allow the axis of stub pins 34 to be inclined accordingly to the anatomical requirements of the patient as determined by the surgeon. Cup 14 now includes two portions—portion 64 which is affixed in the patient's bone, and retaining ring portion 74 which carries stub pins 34 and is engageable with portion 64 at a number of locations to provide a plurality of orientations for the axis through pins 34 about which socket bearing 12 rotates. Portion 64 is shaped to accept and hold retaining ring 74 by means of bayonet spaces 68 and lugs 70. Inner spherical surface 72 is continuous with spherical surface 76 of ring 74. Ring 74 carries stub half pin members 34, has recesses 38 and bayonet lugs 78. A particularly preferred construction for portion 64, and, in particular, for the exterior surface of this portion, is disclosed in copending U.S. patent application Ser. No. 553,519 to Douglas G. Noiles, filed simultaneously herewith and assigned to the assignee of the present application. The pertinent portions of this application are incorporated herein by reference.

With the embodiment shown in FIGS. 6–8, the portion 64 of cup 14 is implanted in the patient's bone by conventional techniques, or, most preferably, by the techniques described in the above-referenced copending application to Douglas G. Noiles. Ball 10 and bearing 12 are assembled into retaining ring 74 after stem 18 of arm 30 has been implanted in, for example, the patient's femur, the assembly procedure being the same as that described above with reference to FIG. 3 except that protuberance 28 is compressed only once it contacts the back surface of ring 74. The sub-assembly of ball 10, bearing 12 and retaining ring 74 is then inserted into portion 64 in any of the several angular positions the bayonet lug fittings will permit. A fraction of a turn in either direction will engage the lugs 78 of ring 74 under lugs 70 of portion 64. Alternatively, lugs 78 can be beveled at either their right or left hand leading edges so that insertion by rotation in only one direction is facilitated, e.g., clockwise rotation. The engagement of bayonet lugs 78 and 70 is locked by conventional means, such as by one or more pins 80. Holes 79 and 81 for such locking pins can be precisely made in the cooperating parts at the time of manufacture. Although only one hole 81 is shown in FIGS. 6 and 7, a hole would normally be drilled at each bayonet space 68 so that ring 74 can be locked in place for any of its possible orientations.

An embodiment of the present invention similar to that shown in FIGS. 6–8 but employing the system disclosed in the DeCarlo patent application referred to above is shown in FIGS. 15–20. In this embodiment, spherical surface 72 has associated therewith pin or projection 50. This projection is located at the geometric pole of the spherical cavity formed by spherical surfaces 72 and 76. As shown in the figures, pin 50 has sloping sides 60.

Projection 50, in combination with aperture 13 formed in outer surface 22 of bearing member 12, serves to constrain the rotation of bearing 12 so as to prevent the bearing from being rotated out of the spherical cavity once the joint is assembled and to limit the rotation of the bearing so as to keep neck 16 just out of contact with the rim of ring 74, e.g., on the order of a half a millimeter above the rim. In particular, bearing 12 can rotate only to the point where polar pin 50 and one of the end walls 52 or 54 of aperture 13 are in engagement. As discussed below, this constrained condition for bearing 12 occurs automatically as the joint is assembled without any additional assembly steps. Also, the constraining of socket bearing 12 within the joint is accomplished irrespective of the angular orientation chosen for retaining ring 74 with respect to body portion 64 of cup 14.

Figure 19:
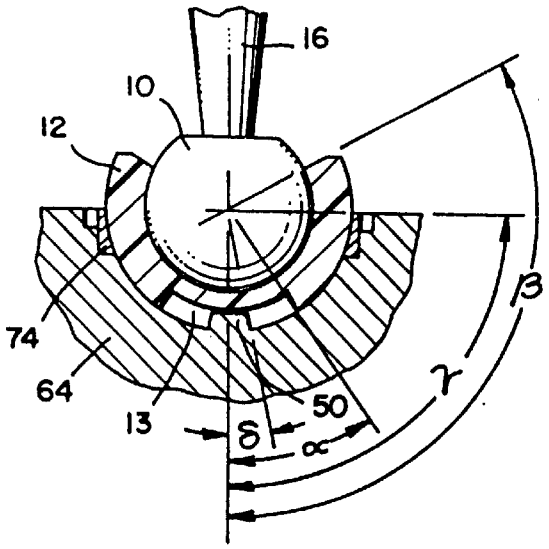
FIGS. 19 and 20 are schematic diagrams illustrating the relationships between the angular extents of the various components of the artificial joint shown in FIGS. 15–17.
Figure 20:
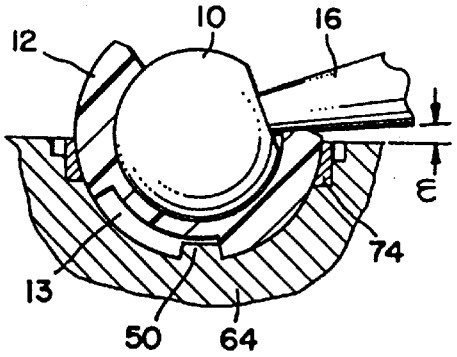
Figure 21:
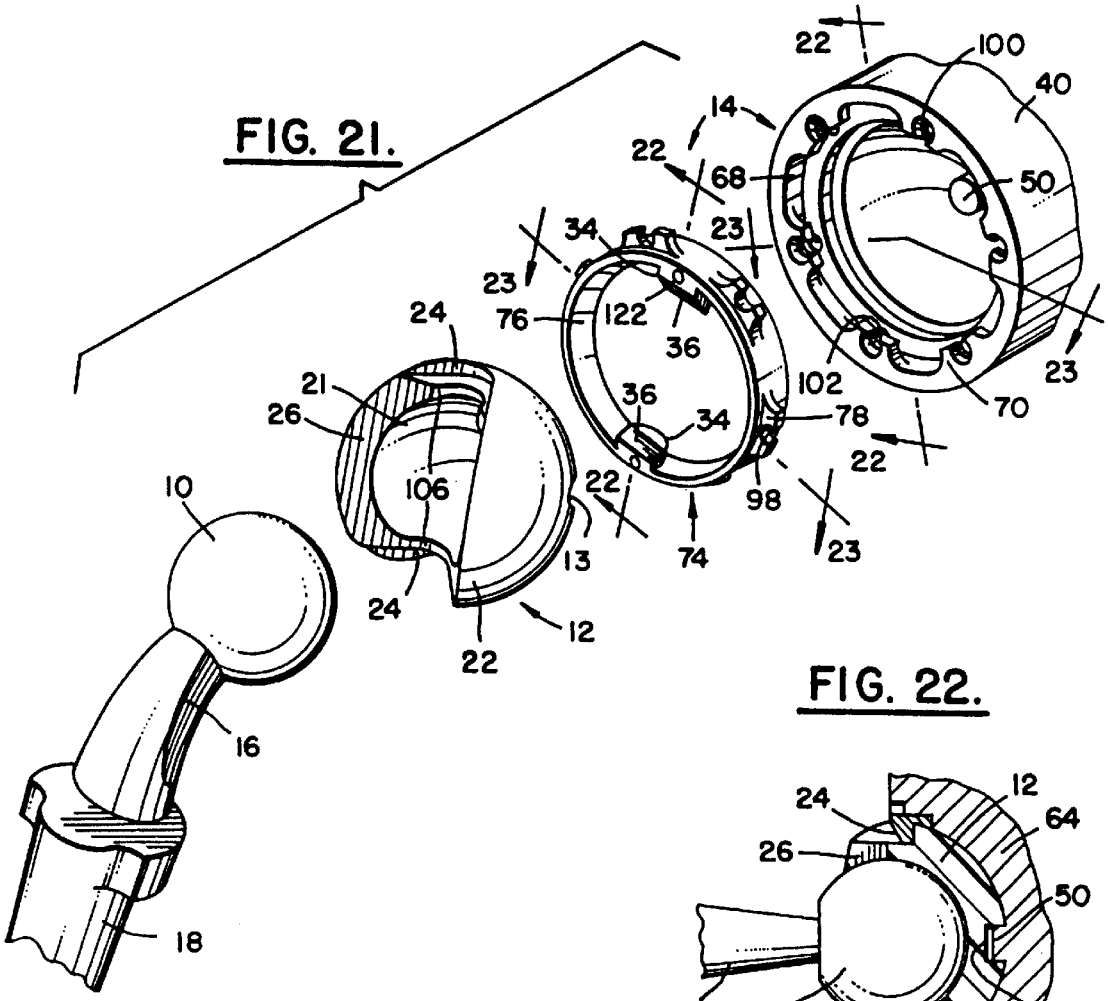
FIG. 21 is an exploded view of an artificial joint of the semi-constrained type embodying the present invention and employing a system of the type disclosed in the DeCarlo patent application referred to above to limit the range of motion of the socket bearing within the joint.
Figure 22:
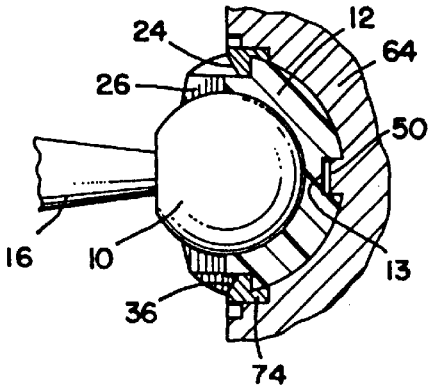
FIG. 22 is a cross-sectional view along lines 22—22 in FIG. 21.
Figure 23:
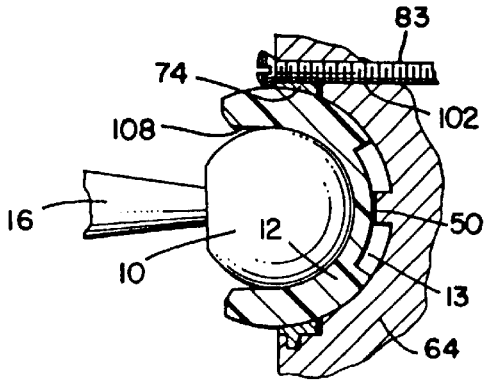
FIG. 23 is a cross-sectional view along lines 23—23 in FIG. 21.

Aperture 13 has a long axis parallel to side walls 56 and 58 and a short axis at 90° to side walls 56 and 58. The angular extent of aperture 13 along its short axis is sufficient to accommodate polar pin 50. The angular extent of aperture 13 along its long axis determines the range of motion of socket bearing 12. As discussed above, a particularly preferred range motion for bearing 12 is one in which neck 16 is kept just out of contact with ring 74. In this case, as shown in FIGS. 19–20, the angular extent ($\alpha$) of aperture 13 along its long axis is determined by: (1) the maximum angular extent ($\beta$) of socket bearing 12: (2) the minimum angular extent ($\gamma$) of cup 14; (3) the angular extent ($\delta$) of polar pin 50; and the angular offset ($\epsilon$) of neck 16 from cup 14. In particular, the angular extent of aperture 13 is given by:

$$\alpha=\beta+\delta-\gamma-\epsilon.$$

Similar relationships can be derived for other desired ranges of motion for socket bearing 12.

The placement of pin 50 at the pole of the spherical cavity formed by surfaces 72 and 76 allows retaining ring 74 to be inserted into body portion 64 of cup 14 in any of the possible orientations provided by the mating of bayonet lugs 78 with bayonet lugs 70. That is, once socket bearing 12 is rotated about stub pins 34 until at least some portion of aperture 13 is located over the central axis of ring 74, ring 74 can be mated with body portion 64 in any of their possible relative orientations, because, for each of those orientations, aperture 13 will slip over projection 50. Since placing aperture 13 about pin 50 results in the restraining of bearing 12 in cup 14 without any further action by the surgeon, it can be seen that assembly of the joint automatically produced the desired restraining function.

A typical sequence of steps for implanting the prosthesis of the embodiment shown in FIGS. 15–20 in a patient are as follows. Stem 18 of arm 30 is implanted by conventional techniques in, for example, the patient's femur bone. Body portion 64 of cup 14 can also be implanted by conventional techniques, or, most preferably, by the techniques described in the above-referenced copending application to Douglas G. Noiles. Bearing 12 is assembled into ring 74 and then ball 10 is forced into bearing 12. Alternatively, bearing 12 can first be placed on ball 10 and that combination assembled into ring 74. In either case, the sub-assembly of ball 10, bearing 12 and retaining ring 74 is then inserted into body portion 64 in any of the several angular positions the bayonet lug fittings will permit with polar pin 50 sliding into aperture 13. A fraction of a turn in either direction will engage the lugs 78 of ring 74 under lugs 70 of portion 64. Alternatively, as discussed above, lugs 78 can be beveled at either their right or left hand leading edges so that insertion by rotation in only one direction is facilitated, e.g., clockwise rotation. To aid in the rotation of ring 74, the ring can include apertures 122 for engagement with a spanner wrench or the like. Note that because of the polar location of pin 50, ring 74 and its attached bearing 12 can be rotated to engage lugs 78 and 70 irrespective of where pin 50 is located along the length of aperture 13. The engagement of bayonet lugs 78 and 70 is locked by one or more screws 83 which pass through openings 100 and 98 in lugs 70 and 78, respectively, and then through holes 102 to engage the bone into which cup 64 has been implanted.

For hip joints, the possibility of a number of orientations for the axis of rotation of bearing 12 is used to place that axis in an orientation in which the greater required range of motion is aligned approximately with axis P—P. For example, the axis of rotation can be oriented upward in the forward direction to achieve this result. In this way, almost all of the highly repetitive [lead] *load* bearing motions of the joint will occur along or close to this axis. As discussed above, motions along or near to the axis of rotation of bearing 12 consist primarily of ball 10 moving in bearing 12, rather than bearing 12 moving in cup 14. As also discussed above, the frictional torques involved further favor movement of ball 10 in bearing 12. Accordingly, by placing the axis of rotation of bearing 12 in a favorable orientation, most repetitive motion will occur by movement of ball 10. This is an important advantage because it means that the joint will have low friction in that friction increases with the diameter of the moving member and ball 10 has a smaller diameter than bearing 12. Put another way, by orienting the axis of rotation of the bearing 12 in the manner described above, the joint of the present invention for the great majority of motions of the patient's limb exhibits the frictional behavior of a small ball, e.g., a 28 mm ball, while providing a range of motion corresponding to a large ball, e.g., a 42 mm ball.

Figure 9:
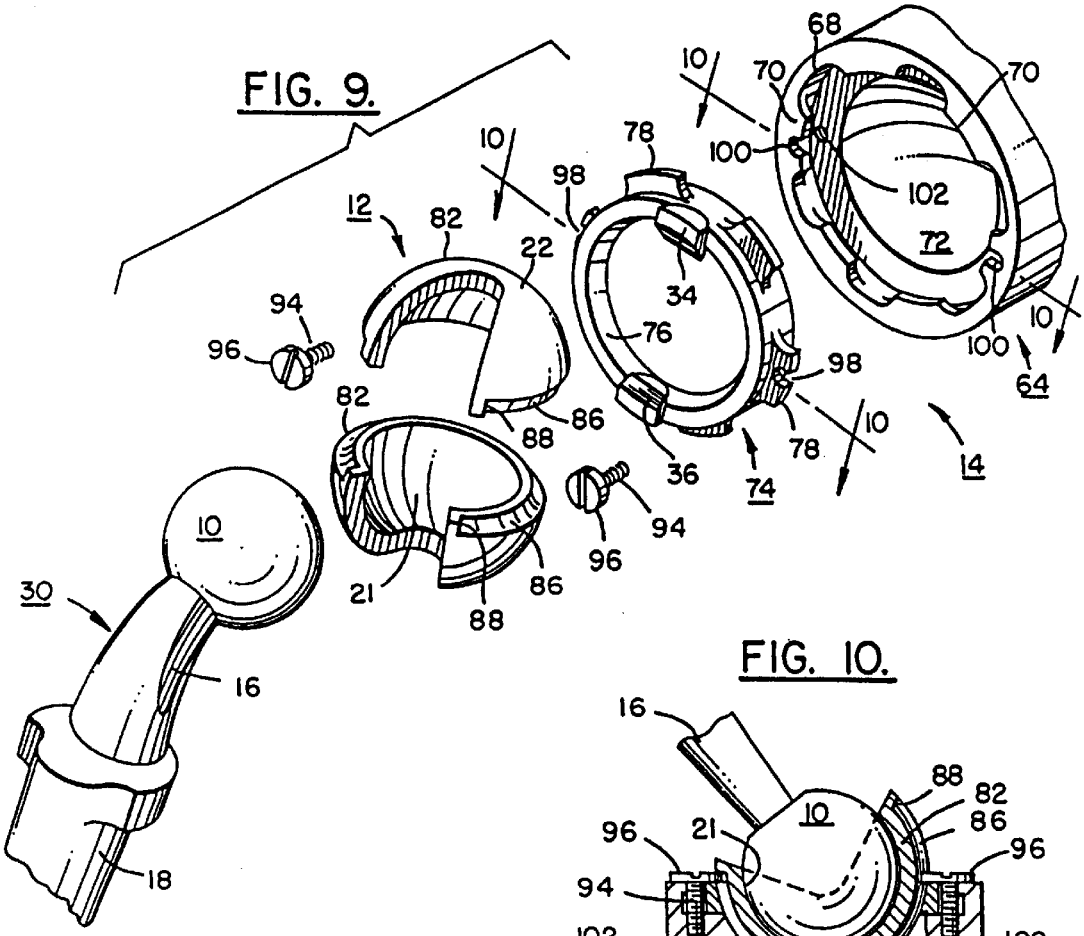
FIG. 9 is an alternate embodiment of the embodiment shown in FIGS. 6–8 wherein a two piece metal socket bearing is used.
Figure 10:
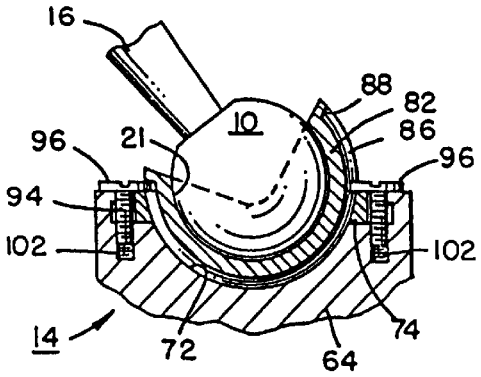
FIG. 10 is a cross-sectional view along lines 10—10 in FIG. 9 after the joint has been assembled.

FIGS. 9 and 10 show another embodiment employing retaining ring 74 in which the socket bearing comprises two metal half bearings 82. A groove 86 is formed along the junction of the bearings and ends short of the edge of the bearing to form shoulders 88. Metal half bearings 82 are brought together to encompass ball 10, and the ball, half bearings, retaining ring 74 and portion 64 of cup 14 are assembled in the same manner as described above in connection with FIGS. 6–8.

Screws 94 having screw heads 96 are conveniently used both to lock lugs 70 and 78 in place and to prevent socket bearing 12 from rotating back out of retaining ring 74. Screw heads 96 ride in groove 86 and engage shoulders 88 when socket bearing 12 has been moved through its full range of motion about stub pins 34. Lugs 70 and 78 have appropriate openings 100 and 98, respectively, to receive screws 94 and allow the screws to be engaged with, in this case, threaded screw holes 102. Although only two openings 100 and two threaded screw holes 102 are shown in FIGS. 9 and 10, such openings and threaded holes would normally be provided at each lug 70 so that ring 74 can be locked in place for any of its possible orientations.

As shown in FIGS. 9 and 10, and most clearly in FIG. 10, screw heads 96 for the present embodiment lie above the plane of the front face of retaining ring 74. So as to provide the same range of motion of socket bearing 12 for this embodiment as for the embodiment of FIGS. 6–8, stub pins 34 also lie above this plane, so that the axis of rotation of socket bearing 12 is in the plane of screw heads 96. For this arrangement, the motion of bearing 12, and thus arm 30, is limited by screw head 96 contacting shoulder 88, rather than by neck 16 contacting retaining ring 74.

Figure 12:
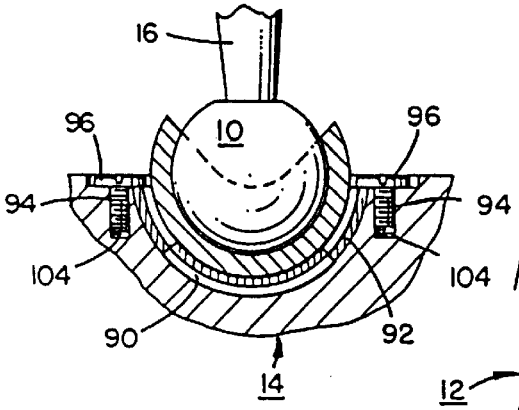
FIG. 12 is a cross-sectional view along lines 12—12 in FIG. 11 after the joint has been assembled.
Figure 11:
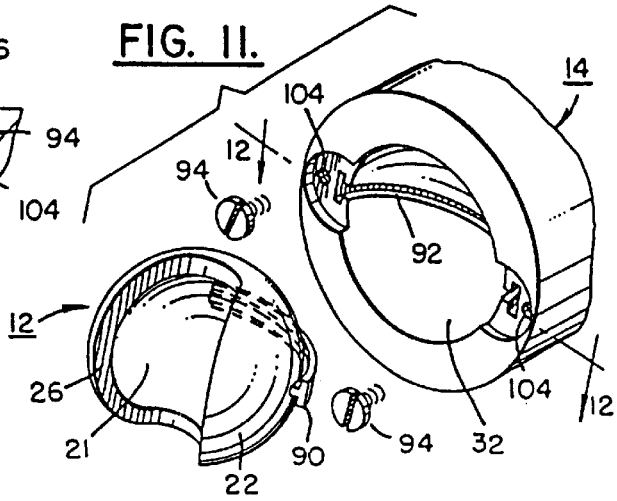
FIG. 11 is an exploded view showing an alternative method for rotatably retaining the socket bearing within the cup.

A further embodiment of the present invention is shown in FIGS. 11 and 12. This embodiment employs means other than half stub pins 34 to define the axis of rotation of socket bearing 12 within cup 14. In particular, a dovetail arrangement is used wherein male portion 90 of the dovetail is attached to socket bearing 12 and female portion 92 of the dovetail is cut into surface 32 of cup 14. Socket bearing 12 and cup 14 are assembled in a manner similar to that shown in FIG. 3. That is, after socket bearing 12 has been placed over ball 10, the ball and socket bearing are moved into cup 14 until the center of ball 10 lies at the center of the cup's spherical cavity. Thereafter, socket bearing 12 is rotated so that male portion 90 and female portion 92 of the dovetail engage with each other. To retain socket bearing 12 within cup 14, screws 94 can be inserted into threaded holes 104 in cup 14 so as to block the outward passage of male portion 90 of the dovetail from cup 14.

Figure 13:
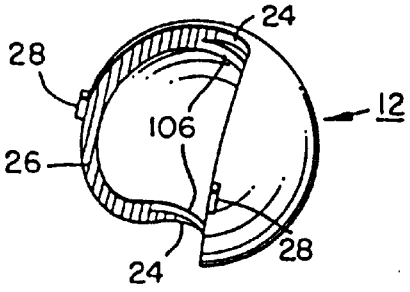
FIGS. 13 and 14 show alternative socket bearings for use with the present invention.
Figure 14:
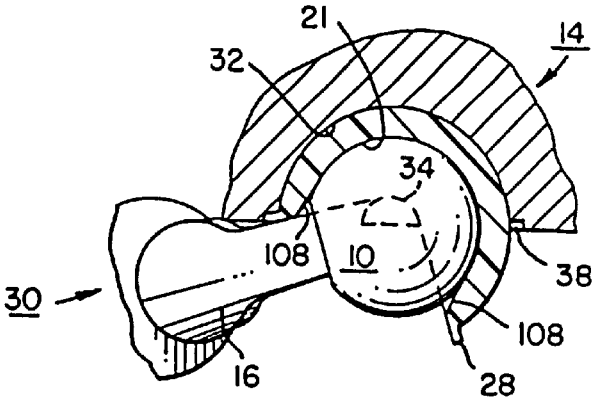
Figure 15:
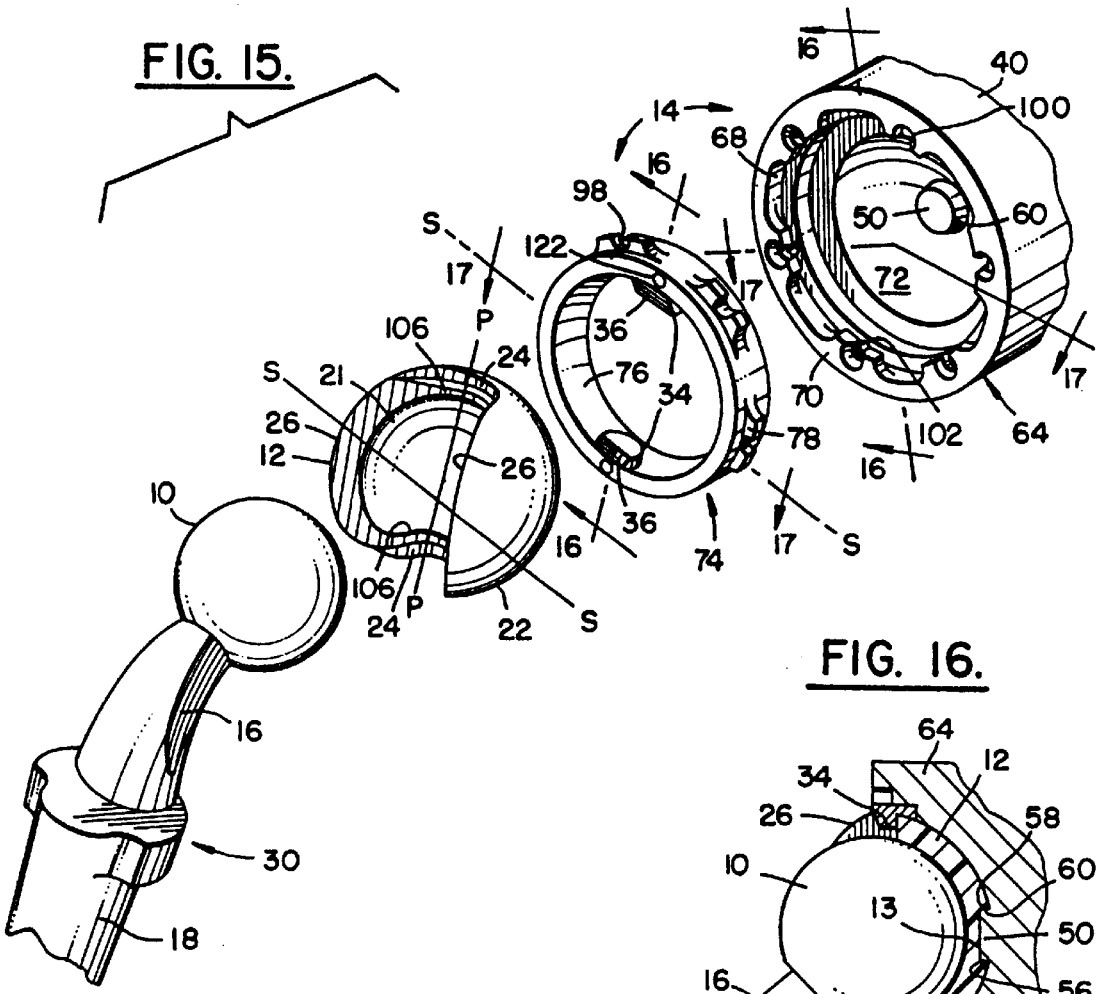
FIG. 15 is an exploded view of an artificial joint similar to that shown in FIGS. 6–8 but employing a system of the type disclosed in the DeCarlo patent application referred to above to limit the range of motion of the socket bearing within the joint.
Figure 16:
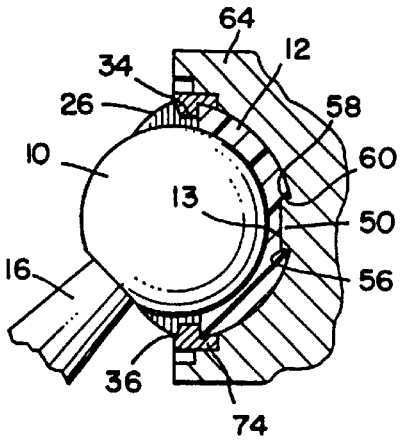
FIG. 16 is a cross-sectional view along lines 16—16 in FIG. 15.
Figure 17:
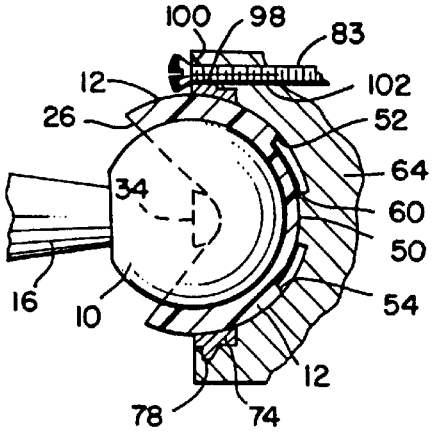
FIG. 17 is a cross-sectional view along lines 17—17 of FIG. 15.
Figure 18:
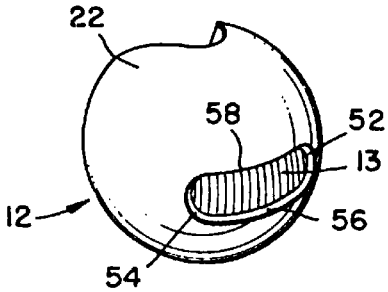
FIG. 18 is a perspective view of the outer surface of the bearing member of FIG. 15.

FIGS. 13 and 14 show alternate socket bearings for use with the present invention.

In FIG. 13, cylindrical surfaces 24 do not extend completely through the wall of bearing 12, but rather stop approximately half way through to leave webs 106. So as to provide as large a range of motion of arm 30 in the plane through lines P—P as possible (see FIG. 2), the webs extend to just above height of stub pins 34 at the end of bevels 36. In this way, as discussed above, the motion of ball 10 in the plane through lines P-P is limited by arm 16 contacting webs 106. The webs, although small, help restrain ball 10 within bearing 12.

FIGS. 14 and 21–23 show embodiments of bearing 12 which do not physically [contrain] *constrain* ball 10. For these embodiments, inner surface 21 of bearing 12 has a cylindrical shape 108 beyond its equator. This provides a semiconstrained type of construction having a greater depth than presently available. Such a bearing can be used with the other components of the present invention to provide the advantages, discussed above, of (1) producing a wider range of motion, e.g., on the order of 135°, and (2) providing a level of friction characteristic of a small ball for the majority of the motions of the patient's limb.

Figure 24:
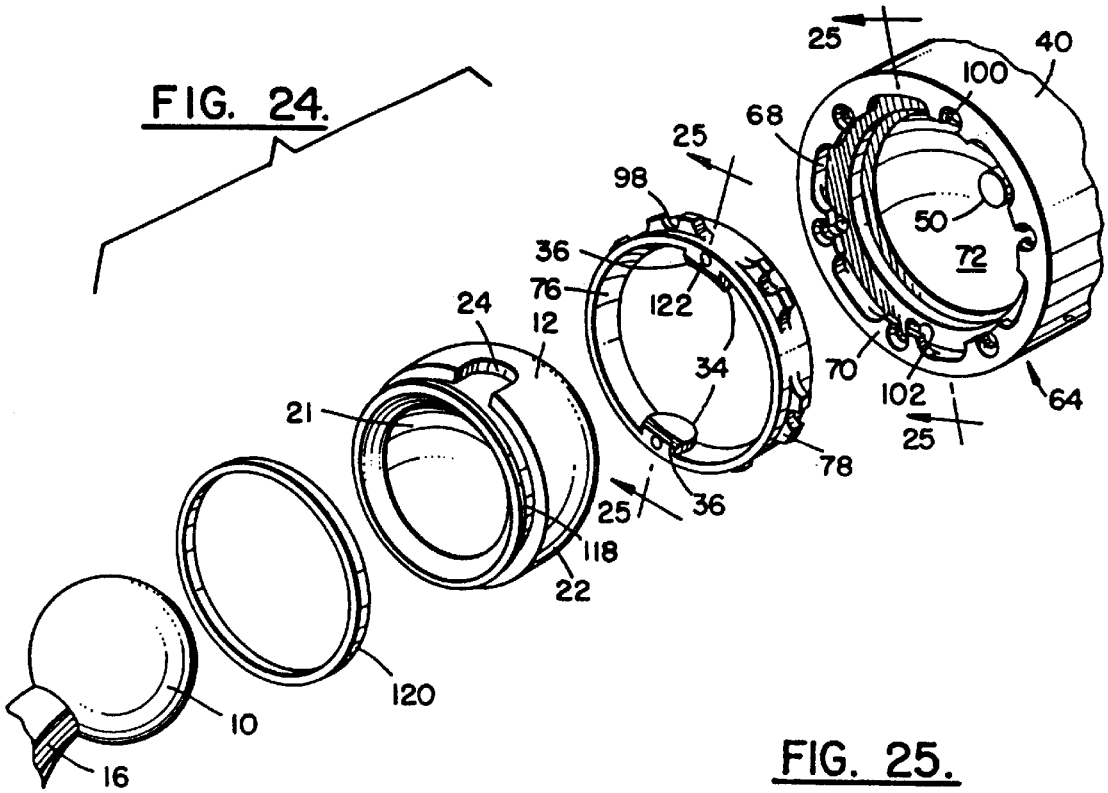
FIG. 24 is an exploded view of an artificial joint of the constrained type constructed in accordance with the present invention and including a metal reinforcing band to increase the amount of force required to dislocate the joint. This embodiment also employs a system of the type disclosed in the DeCarlo patent application referred to above to limit the range of motion of the socket bearing within the joint.
Figure 25:
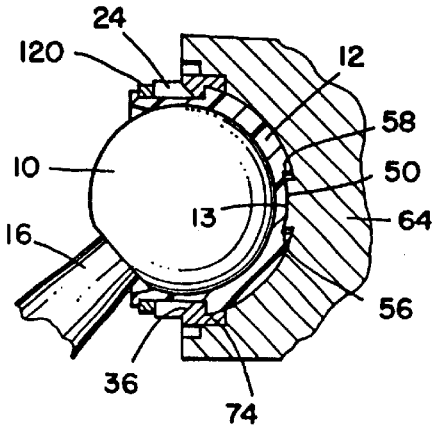
FIG. 25 is a cross-sectional view along lines 25—25 in FIG. 24.
Figure 26:
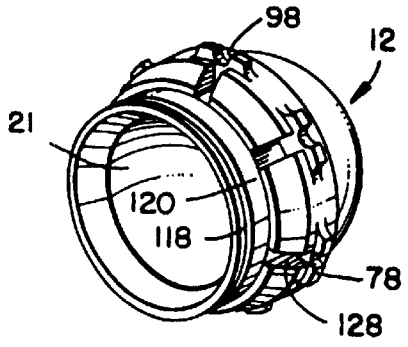
FIG. 26 is a perspective view of a plastic socket bearing constructed in accordance with the present invention and designed to produce a completed joint of the non-rotating, constrained type.
Figure 27:
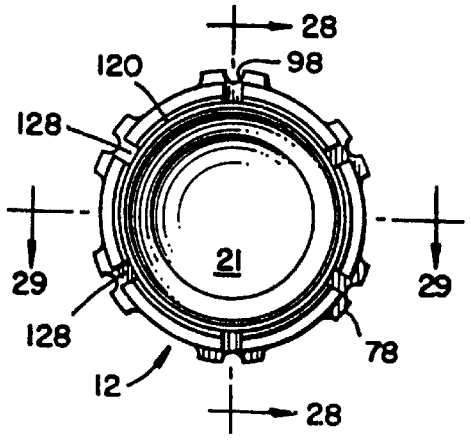
FIG. 27 is a front view of the bearing of FIG. 26.
Figure 28:
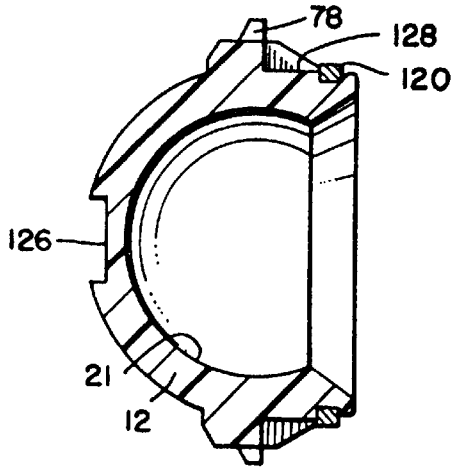
FIG. 28 is a cross-sectional view along lines 28—28 in FIG. 27.
Figure 29:
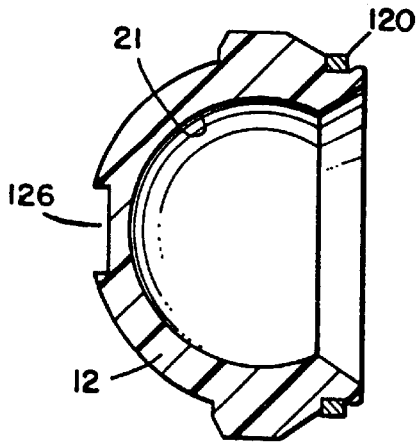
FIG. 29 is a cross-sectional view along lines 29—29 in FIG. 27.
Figure 30:
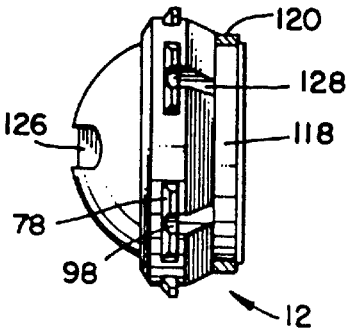
FIG. 30 is a side view of the bearing of FIG. 26.

FIGS. 24–25 show another embodiment of the present invention wherein a plastic bearing 12 is fitted at its rim 118 with a metal reinforcing band 120 to produce a constrained joint able to withstand higher dislocation forces than, for example, the joints including plastic bearings shown in FIGS. 1–8 and 15–20. For this joint, the order of assembly is first to combine bearing 12 with ring 74, then to force the bearing 12 over ball 10 and finally to assemble band 120 to the rim of bearing 12. If the ball portion of the joint has already been implanted in the patient, this assembly order means that band 120 has to be placed over ball 10 before the bearing is mounted onto the ball.

The constructions of FIGS. 6–8, 9–10, 15–20, 21–23 and 24–25 illustrate various *joint* configurations which can be interchangeably connected to body 64 by means of bayonet lugs 70 and 78 on body 64 and ring 74, respectively. These configurations share the common characteristic that bearing 12 is free to rotate about stub pins 34 in the final assembled joint. They differ from one another in the degree of constraint imposed on the ball by the bearing and/or the types of materials used to construct the bearing. Because the bearings are free to rotate, these joints, when applied to hip reconstructions, also share the characteristic that there is a preferred orientation of the joint with respect to the patient's anatomy, namely, an orientation wherein most of the highly repetitive load bearing motions of the joint occur along or close to the axis of rotation of the bearing.

FIGS. 26–34 show further examples of joint components which can be interchangeably connected to body 64 by means of bayonet lugs 70 and 78 on body 64 and, in this case, on bearing 12, respectively. These joint configurations have the common characteristic that bearing 12 is stationary with respect to body 64. As with the joints of the prior examples, these joints differ among themselves in the degree of constraint imposed on the ball by the bearing and/or the types of materials used to construct the bearing.

More particularly, FIGS. 26–30 show a construction of the constrained type employing a plastic socket bearing to which has been added a metal reinforcing band 120 at rim 118 of the bearing so as to increase the bearing's ability to withstand dislocation forces. As shown in the figures, the bearing includes a recess 126 at its pole which allows the bearing to be used with a body 64 which includes a polar pin 50. Of course, if body 64 does not have a polar pin, the bearing need not have recess 126.

Assembly of a completed joint using this bearing is accomplished as follows. First, bearing 12 is forced over ball 10 and band 120 is forced over the bearing's rim 118. If the ball portion of the joint has already been implanted in the patient, band 120 must be placed over ball 10 before bearing is mounted onto the ball. The sub-assembly of ball 10, bearing 12 and reinforcing band 120 is then inserted into body 64 in any of the several angular positions the bayonet lug fittings will permit. Polar pin 50 is received in recess 126 during this process. Since the bearing of FIGS. 26–30 is symmetric and thus does not define a particular orientation with respect to the patient's anatomy, the specific [oritentation] *orientation* of the bearing with respect to body 64 is immaterial. Once placed into body 64, a fraction of a turn in either direction will engage the lugs 78 on the bearing under the lugs 70 of body 64. If desired, as described above, lugs 78 can be beveled at either their right or left hand leading edges so that insertion by rotation in only one direction is facilitated, e.g., clockwise rotation. To aid in the rotation of bearing 12, the bearing can include slots 128 for engagement with a spanner wrench or the like. The engagement of bayonet lugs 78 and 70 is locked by one or more screws 83 which pass through openings 100 and 98 in lugs 70 and 78, respectively, and then through holes 102 in body 64 to engage the bone in which cup 64 has been implanted (see FIGS. 33 and 34).

Figure 31:
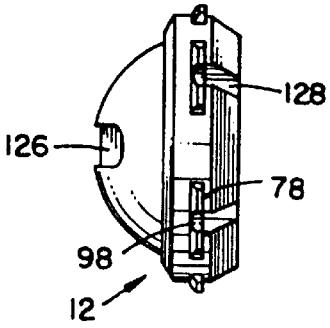
FIG. 31 is a side view of a plastic socket bearing constructed in accordance with the present invention and designed to produce a completed joint of the non-rotating, semi-constrained type.

FIG. 31 shows another plastic socket bearing of essentially the same design as the bearing of FIGS. 26–30 except that rather creating a constrained joint, this bearing produces a semi-constrained joint. That is, the bearing of FIG. 31 does not encompass more than one half of ball 10 and thus does not constrain the ball within the joint. Assembly of a joint using this bearing simply involves inserting and locking the bearing in body 64 using bayonet lugs 78 and one or more bone screws, and then placing ball 10 into bearing 12 using the standard techniques employed in semi-constrained surgical reconstructions.

Figure 32:
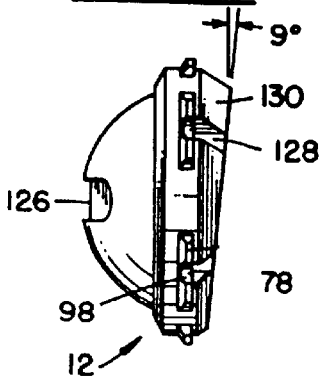
FIG. 32 is a side view of a plastic socket bearing similar to the bearing of FIG. 31 but including a lip to help restrain dislocations of the completed joint.

FIG. 32 shows another plastic socket for use in a semi-constrained reconstruction, in this case with an added lip 130 to help restrain dislocations of ball 10 from the bearing. The lip can be conveniently formed by gradually sloping the front surface of the bearing as shown in FIG. 32. A suitable slope is on the order of 9°. Unlike the symmetric bearings of FIGS. 26–31, the bearing of FIG. 32 does define an orientation between itself and the patient's anatomy. Accordingly, when installing this bearing, the surgeon will choose an orientation of the bearing with respect to body 64 which will place lip 130 in the most advantageous position to inhibit dislocation. Other than this orientation step, the installation procedure for a joint using this bearing is identical to the installation procedure described above for the bearing of FIG. 31.

Figure 33:
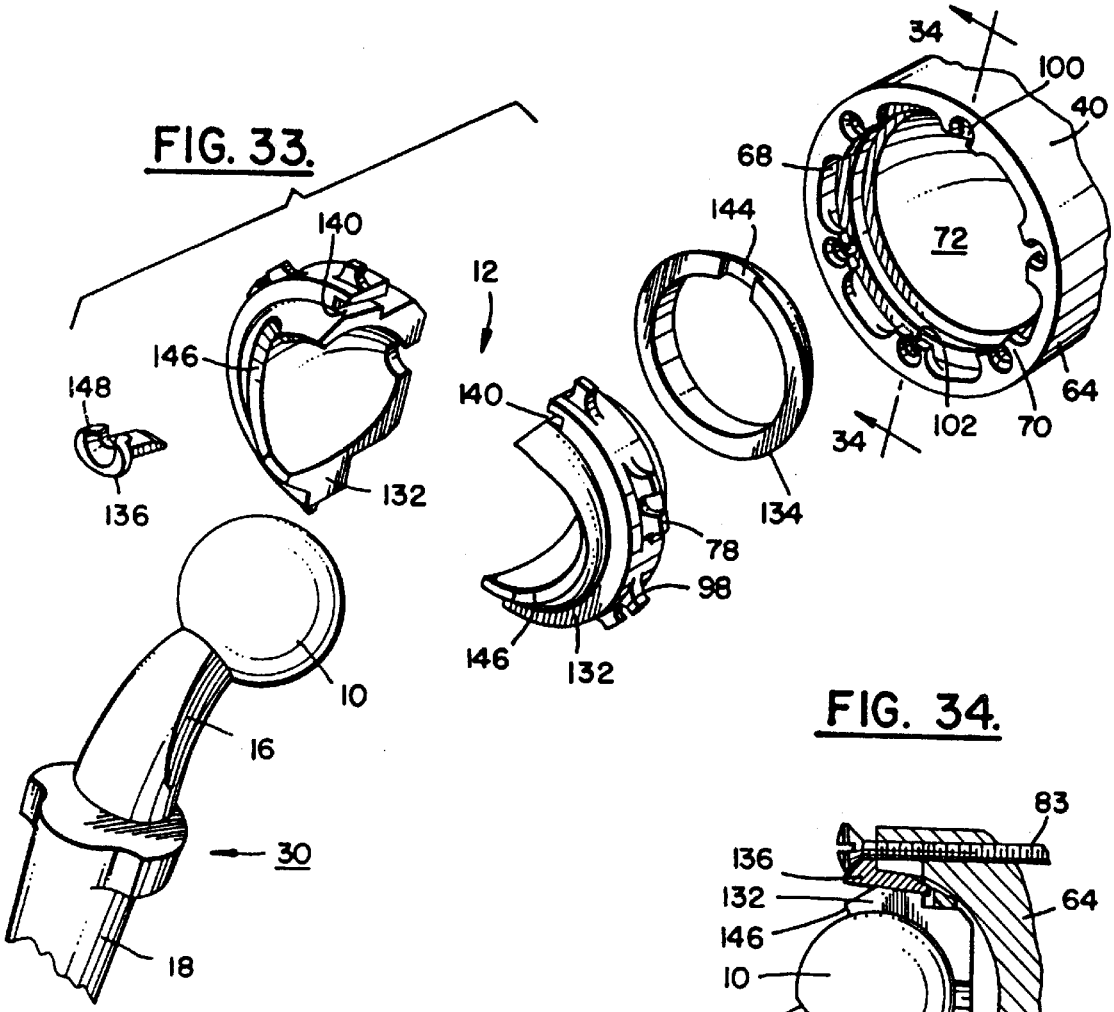
FIG. 33 is an exploded view of an artificial joint of the non-rotating, constrained type constructed in accordance with the present invention and employing a metal socket bearing.
Figure 34:
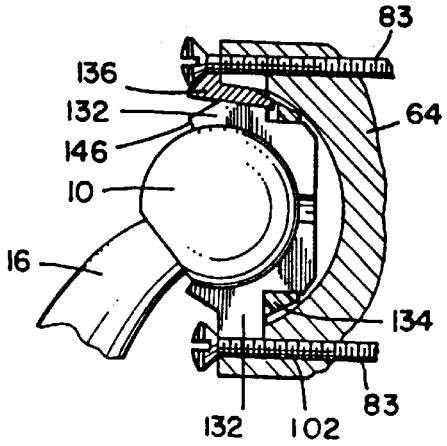
FIG. 34 is a cross-sectional view along lines 34—34 in FIG. 33.

FIGS. 33–34 show a non-rotating, constrained joint employing a metal bearing. The bearing is composed of two half-bearings 132 which carry bayonet lugs 78. During assembly of the joint, half-bearings 132 are placed about ball 10 and then held in place by plastic retaining ring 134. The sub-assembly of ball 10 and bearing 12 is then inserted into body 64 in basically the same manner as the bearing of FIGS. 26–30. Typically, body 64 is made of a titanium alloy, e.g., an alloy containing 6% aluminum and 4% vanadium (see ASTM Spec. No. F136-79), while bearing halves 132, as well as ball 10, are made of a cobalt-chromium alloy. As is known in the art, titanium alloys are not wear resistant when in moving contact with cobalt-chromium alloys and thus continual relative movement between a titanium part and a cobalt-chromium part will eventually result in significant wearing of the titanium part.

To prevent such wearing due to relative movement, the joint of FIGS. 33–34 includes wedge 136 which serves to force half-bearings 132 into tight engagement with body 64. Wedge 136 passes through slot 140 in bearing 12 and into recess 144 in retaining ring 134. The head portion 148 of the wedge is struck with a hammer or the like after bearing 12 has been positioned in body 64. The hammer blow forces the bearing halves apart and locks them into position with respect to body 64.

To prevent wedge 136 from working loose over time, bone screw 83 can be used to engage the head of the wedge as shown in FIG. 34. So that the wedge can easily be removed, e.g., during replacement of the bearing by a different type of bearing, the underside of head 148 can be cambered so that the wedge can readily be pried away from the bearing. Because the wedging process causes the bearing halves 132 to move away from each other by pivoting about their point of contact opposite the location of the wedge, the interior surfaces of the bearing halves can be contoured so that a spherical surface is formed only after the outward movement of the bearing halves. Alternatively, the interior surfaces can be made spherical since the slight amount of play between ball 10 and bearing 12 caused by the wedging process can normally be tolerated in the completed joint.

As can be seen most clearly in FIG. 33, edge 146 of bearing 12 is not symmetric. More particularly, this edge allows ball 10 to move through one angular range in the plane of FIG. 34 and a relatively larger angular range in the plane orthogonal to the plane of FIG. 34. Accordingly, when installing this bearing, the surgeon will choose an orientation of bearing 12 in body 64 which causes the plane corresponding to the relatively larger range of angular motion to coincide as closely as possible with the plane in which the patient's limb normally moves through its largest range of angular motion.

The nine joint configurations shown in FIGS. 6–8, 9–10, 15–20, 21–23, 24–25, 26–30, 31, 32, and 33–34 are each interchangeable with each other. This interchangeability gives the surgeon the flexibility of being able to choose, in situ, any of these configurations or any other configuration constructed to mate with body 64. In this way, a more perfect match between the requirements of the patient and the characteristics of the artificial joint is achieved.

From the foregoing, it is evident that the present invention provides a constrained ball and socket joint which has a range of motion greater than that generally available in artificial joints whether of the constrained or semi-constrained type. Moreover, the present invention provides an artificial joint which can be oriented in the patient to provide low friction movement of a ball of relatively small diameter for most of the patient's repetitive activities. The limiting factor in providing the increased range of motion is the outside diameter of the bearing. Accordingly, within anatomical limits, it is advantageous for the bearing outside diameter to be as large as possible.

The increased range of motion provided by the present invention allows the patient to move his limb further than heretofore possible in constrained joints without the arm of the prosthesis impinging on the edge of the bearing. Accordingly, there is less likelihood of dislocation when plastic bearings are used or disruption of the bond between the fixation element and the bone to which it is attached when metal bearings are used. Moreover, when the range of motion of the present joint is greater than the patient can take advantage of, the surgeon is afforded greater latitude for variation in the orientation of the prosthetic components with respect to the patient's anatomy without the hazard of impingement.

In addition to these orientability and range of motion aspects, the present invention, by providing interchangeable sockets, also gives the surgeon the ability to select the most appropriate prosthesis for the patient's specific requirements both during the initial operation and, if necessary, during re-operations. As demonstrated by the examples described above, the surgeon, in accordance with the present invention, has a diverse family of ball and socket joints to choose from extending from semi-constrained, fixed bearings made of plastic through constrained, rotating bearings made of metal, as well as a variety of configurations in between. This choice plainly permits a better match between the requirements of the patient and the capabilities of the prosthesis.

Numerous modifications and variations of the present invention are possible in light of the above teachings. For example, ball 10, socket bearing 12 and retaining ring 74 can be provided to the surgeon as a unit, rather than being assembled at the surgical site. Also, metal socket bearings can be used with one piece cups, such as cup 14 shown in FIG. 1, rather than with a retaining ring as shown in FIGS. 9 and 10. Furthermore, various connecting means other than bayonet spaces and lugs can be used to attach ring 74 or bearing 12 to body 64, such as, snap rings. In addition, a variety of socket bearings other than those specifically illustrated herein can be used to make up the family of interchangeable bearings supplied to the surgeon. It is therefore understood that within the scope of the appended claims, the invention may be practiced otherwise than as specifically described.

What is claimed is:

1. A ball and socket joint for implantation in a patient's body comprising a ball portion and a socket portion, the ball portion including:

a ball; and first fixation means for attachment to a first bony structure, said fixation means being connected to said ball *by a neck element*; and the socket portion including:

a bearing [for receiving] *having an inner bearing surface configured to receive and surround a portion of* the ball *wherein the ball in combination with the neck element are free to move within the bearing in a plurality of directions*;

second fixation means for attachment to a second bony structure, said second fixation means having a cavity for receiving the bearing, said cavity having an opening defining a *first* plane through which the bearing enters the cavity; and means for securing the bearing to the second fixation means in any one of a plurality of selectable orientations after the second fixation means has been attached to the second bony structure, said plurality of selectable orientations being angularly [displace] *displaced* from one another about an axis which is perpendicular to the *first* plane [defined by the opening of the cavity of the second fixation means];

the bearing [being] *having a configuration which is* non-symmetric with regard to rotation about said axis [and] *such that the angular range of motion of the ball with the neck element within the bearing relative to the axis is smaller in at least one first direction than in at least one other direction,* said lack of symmetry making at least one of the selectable angular orientations of the bearing more preferred for physiological reasons than others of said angular orientations, said means for securing allowing said bearing to be secured to said second fixation means in such a preferred orientation after said second fixation means has been attached to the second bony structure.

2. The ball and socket joint of claim 1 wherein the means for securing comprises bayonet spaces and lugs.

3. The ball and socket joint of claim 1 wherein the means for securing includes two coaxial pin members and the bearing includes two coaxial cylindrical surfaces which receive the pin members, the pin members and the cylindrical surfaces allowing the bearing to rotate within the cavity of the second fixation means about a single axis, said single axis being orthogonal to the axis which defines the plurality of selectable angular orientations, the orientation of the single axis with respect to the anatomy of the patient's body making at least one of the selectable angular orientations of the bearing more preferred for physiological reasons than others of said angular orientations, *said at least one first direction being orthogonal to the single axis.*

4. The ball and socket joint of claim 1 wherein the bearing includes a lip to restrain dislocations of the ball from the bearing, the orientation of said lip with respect to the anatomy of the patient's body making at least one of the selectable angular orientations of the bearing more preferred for physiological reasons than others of said angular orientations, *said at least one first direction being in the direction of said lip.*

5. A prosthesis for implantation in a patient's body comprising:

a bearing [for receiving] *having an inner bearing surface configured to receive and surround a portion of* the ball [portion] of a ball and socket joint, *said ball being connected to a neck element and the ball in combination with the neck element being free to move within the bearing in a plurality of directions in the assembled joint*;

fixation means for attachment to a bony structure, said fixation means having a cavity for receiving the bearing, said cavity having an opening defining a *first* plane through which the bearing enters the cavity; and means for securing the bearing to the fixation means in any one of a plurality of selectable orientations after the fixation means has been attached to the bony structure, said plurality of selectable orientations being angularly displaced from one another about an axis which is perpendicular to the *first* plane [defined by the opening of the cavity of the fixation means];

the bearing [being] *having a configuration which is* non-symmetric with regard to rotation about said axis [and] *such that, in the assembled joint, the angular range of motion of the ball with the neck element within the bearing relative to the axis is smaller in at least one first direction than in at least one other direction,* said lack of symmetry making at least one of the selectable angular orientations of the bearing more preferred for physiological reasons than others of said angular orientations, said means for securing allowing said bearing to be secured to said fixation means in such a preferred orientation after said fixation means has been attached to the bony structure.

6. The prosthesis of claim 5 wherein the means for securing comprises bayonet spaces and lugs.

7. The prosthesis of claim 5 wherein the means for securing includes two coaxial pin members and the bearing includes two coaxial cylindrical surfaces which receive the pin members, the pin members and the cylindrical surfaces allowing the bearing to rotate within the cavity of the fixation means about a single axis, said single axis being orthogonal to the axis which defines the plurality of selectable angular orientations, the orientation of the single axis with respect to the anatomy of the patient's body making at least one of the selectable angular orientations of the bearing more preferred for physiological reasons than others of said angular orientations, *said at least one first direction being orthogonal to the single axis.*

8. The prosthesis of claim 5 wherein the bearing includes a lip to restrain dislocations of the ball from the bearing, the orientation of said lip with respect to the anatomy of the patient's body making at least one of the selectable angular orientations of the bearing more preferred for physiological reasons than others of said angular orientations, *said at least one first direction being in the direction of said lip.*

*9. A ball and socket joint for implantation in a patient's body comprising a ball portion and a socket portion,*

*the ball portion including:*

*a ball; and*

*first fixation means for attachment to a first bony structure, said fixation means being connected to said ball; and*

*the socket portion including:*

*a bearing for receiving the ball;*

*second fixation means for attachment to a second bony structure, said second fixation means having a cavity for receiving the bearing, said cavity having an opening defining a plane through which the bearing enters the cavity; and*

*means for securing the bearing to the second fixation means in any one of a plurality of selectable orientations after the second fixation means has been attached to the second bony structure, said plurality of selectable orientations being angularly displaced from one another about an axis which is perpendicular to the plane defined by the opening of the cavity of the second fixation means, said means for securing comprising bayonet spaces and lugs;*

*the bearing being non-symmetric with regard to rotation about said axis and said lack of symmetry making at least*

*one of the selectable angular orientations of the bearing more preferred for physiological reasons than others of said angular orientations, said means for securing allowing said bearing to be secured to said second fixation means in such a preferred orientation after said second fixation means has been attached to the second bony structure.*

*10. A ball and socket joint for implantation in a patient's body comprising a ball portion and a socket portion,*

*the ball portion including:*

*a ball; and*

*first fixation means for attachment to a first bony structure, said fixation means being connected to said ball; and*

*the socket portion including:*

*a bearing for receiving the ball;*

*second fixation means for attachment to a second bony structure, said second fixation means having a cavity for receiving the bearing, said cavity having an opening defining a plane through which the bearing enters the cavity; and*

*means for securing the bearing to the second fixation means in any one of a plurality of selectable orientations after the second fixation means has been attached to the second bony structure, said plurality of selectable orientations being angularly displaced from one another about an axis which is perpendicular to the plane defined by the opening of the cavity of the second fixation means;*

*the bearing being non-symmetric with regard to rotation about said axis and said lack of symmetry making at least one of the selectable angular orientations of the bearing more preferred for physiological reasons than others of said angular orientations, said means for securing allowing said bearing to be secured to said second fixation means in such a preferred orientation after said second fixation means has been attached to the second bony structure, the means for securing including two coaxial pin members and the bearing including two coaxial cylindrical surfaces which receive the pin members, the pin members and the cylindrical surfaces allowing the bearing to rotate within the cavity of the second fixation means about a single axis, said single axis being orthogonal to the axis which defines the plurality of selectable angular orientations, the orientation of the single axis with respect to the anatomy of the patient's body making at least one of the selectable angular orientations of the bearing more preferred for physiological reasons than others of said angular orientations.*

*11. A ball and socket joint for implantation in a patient's body comprising a ball portion and a socket portion,*

*the ball portion including:*

*a ball; and*

*first fixation means for attachment to a first bony structure, said fixation means being connected to said ball; and*

*the socket portion including:*

*a bearing for receiving the ball;*

*second fixation means for attachment to a second bony structure, said second fixation means having a cavity for receiving the bearing, said cavity having an opening defining a plane through which the bearing enters the cavity; and*

*means for securing the bearing to the second fixation means in any one of a plurality of selectable orientations after the second fixation means has been attached to the second bony structure, said plurality of selectable orientations being angularly displaced from one another about an axis which is perpendicular to the plane defined by the opening of the cavity of the second fixation means;*

*the bearing being non-symmetric with regard to rotation about said axis and said lack of symmetry making at least one of the selectable angular orientations of the bearing more preferred for physiological reasons than others of said angular orientations, said means for securing allowing said bearing to be secured to said second fixation means in such a preferred orientation after said second fixation means has been attached to the second bony structure, the bearing including a lip to restrain dislocations of the ball from the bearing, the orientation of said lip with respect to the anatomy of the patient's body making at least one of the selectable angular orientations of the bearing more preferred for physiological reasons than others of said angular orientations.*

*12. A prosthesis for implantation in a patient's body comprising:*

*a bearing for receiving the ball portion of a ball and socket joint;*

*fixation means for attachment to a bony structure, said fixation means having a cavity for receiving the bearing, said cavity having an opening defining a plane through which the bearing enters the cavity; and*

*means for securing the bearing to the fixation means in any one of a plurality of selectable orientations after the fixation means has been attached to the bony structure, said plurality of selectable orientations being angularly displaced from one another about an axis which is perpendicular to the plane defined by the opening of the cavity of the fixation means, said means for securing comprising bayonet spaces and lugs;*

*the bearing being non-symmetric with regard to rotation about said axis and said lack of symmetry making at least one of the selectable angular orientations of the bearing more preferred for physiological reasons than others of said angular orientations, said means for securing allowing said bearing to be secured to said fixation means in such a preferred orientation after said fixation means has been attached to the bony structure.*

*13. A prosthesis for implantation in a patient's body comprising:*

*a bearing for receiving the ball portion of a ball and socket joint;*

*fixation means for attachment to a bony structure, said fixation means having a cavity for receiving the bearing, said cavity having an opening defining a plane through which the bearing enters the cavity; and*

*means for securing the bearing to the fixation means in any one of a plurality of selectable orientations after the fixation means has been attached to the bony structure, said plurality of selectable orientations being angularly displaced from one another about an axis which is perpendicular to the plane defined by the opening of the cavity of the fixation means;*

*the bearing being non-symmetric with regard to rotation about said axis and said lack of symmetry making at least one of the selectable angular orientations of the bearing more preferred for physiological reasons than others of said angular orientations, said means for securing allowing said bearing to be secured to said fixation means in such a preferred orientation after said fixation means has been attached to the bony structure, the means for securing including two coaxial pin members and the bearing including two coaxial cylindrical surfaces which receive the pin members, the pin*

*members and the cylindrical surfaces allowing the bearing to rotate within the cavity of the fixation means about a single axis, said single axis being orthogonal to the axis which defines the plurality of selectable angular orientations, the orientation of the single axis with respect to the anatomy of the patient's body making at least one of the selectable angular orientations of the bearing more preferred for physiological reasons than others of said angular orientations.*

*14. A prosthesis for implantation in a patient's body comprising:*

*a bearing for receiving the ball portion of a ball and socket joint;*

*fixation means for attachment to a bony structure, said fixation means having a cavity for receiving the bearing, said cavity having an opening defining a plane through which the bearing enters the cavity; and*

*means for securing the bearing to the fixation means in any one of a plurality of selectable orientations after the fixation means has been attached to the bony structure, said plurality of selectable orientations being angularly displaced from one another about an axis which is perpendicular to the plane defined by the opening of the cavity of the fixation means;*

*the bearing being non-symmetric with regard to rotation about said axis and said lack of symmetry making at least one of the selectable angular orientations of the bearing more preferred for physiological reasons than others of said angular orientations, said means for securing allowing said bearing to be secured to said fixation means in such a preferred orientation after said fixation means has been attached to the bony structure, the bearing including a lip to restrain dislocations of the ball from the bearing, the orientation of said lip with respect to the anatomy of the patient's body making at least one of the selectable angular orientations of the bearing more preferred for physiological reasons than others of said angular orientations.*

* * * * *